United States Patent
Nakano et al.

(10) Patent No.: US 10,323,254 B2
(45) Date of Patent: Jun. 18, 2019

(54) METHOD FOR REGULATING PLANT GROWTH

(71) Applicant: RIKEN, Wako-shi, Saitama (JP)

(72) Inventors: Takeshi Nakano, Wako (JP); Tadao Asami, Wako (JP); Ayumi Yamagami, Wako (JP); Hiroyuki Osada, Wako (JP)

(73) Assignee: RIKEN, Wako-Shi, Saitama (JP)

( * ) Notice: Subject to any disclaimer, the term of this patent is extended or adjusted under 35 U.S.C. 154(b) by 9 days.

(21) Appl. No.: 15/546,613

(22) PCT Filed: Jan. 25, 2016

(86) PCT No.: PCT/JP2016/052052
§ 371 (c)(1),
(2) Date: Jul. 26, 2017

(87) PCT Pub. No.: WO2016/121707
PCT Pub. Date: Aug. 4, 2016

(65) Prior Publication Data
US 2018/0030468 A1    Feb. 1, 2018

Related U.S. Application Data

(60) Provisional application No. 62/108,327, filed on Jan. 27, 2015.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8298* (2013.01); *Y02A 40/146* (2018.01)

(58) Field of Classification Search
None
See application file for complete search history.

(56) References Cited

PUBLICATIONS

GenBank Accession No. NM_001203187, May 26, 2011 (Year: 2011).*
GenEmbl Accession No. HM001190116, Aug. 1, 2011 (Year: 2011).*
Ha et al, Plant Cell Physiol., 2004, vol. 45, No. 10, pp. 1461-1370 (Year: 2004).*
Norberg et al, Development, 2005, vol. 132, pp. 2203-2213 (Year: 2005).*
GenEmbl Accession No. HM991172, Aug. 1, 2011 (Year: 2011).*
Asami et al., "The Influence of Chemical Genetics on Plant Science: Shedding Light on Functions and Mechanism of Action of Brassinosteroids Using Biosynthesis Inhibitors", J Plant Growth Regulation (2003), 22, pp. 336-349.
Ha et al., "Blade-On-Petiole1 Encodes a BTB/POZ Domain Protein Required for Leaf Morphogenesis in *Arabidopsis thaliana*", Plant Cell Physiol., vol. 45, No. 10, pp. 1361-1370, 2004.
International Search Report for PCT/JP2016/052052 (PCT/ISA/210) dated Apr. 12, 2016.
Nakano et al., "Brassinosteroid Joho Dentatsu Tanpakushitsu BSS1 no 'Shugo to Kakusan' ni yoru Shokubutsu Kusatake Seigyo Kiko Shokubutsu Chemical Biology ga Akiraka ni shita Aratana Tanpakushitsu no Dynamics", Kagaku to Seibutsu, vol. 53, No. 11, Oct. 20, 2015, pp. 734-736.
Shimada et al., "Analysis for brassinosteroid signaling factor BSS1", The Japanese Society for Chemical Regulation of Plants, Oct. 2014, vol. 49, p. 54.
Shimada et al., Formation and Dissociation of the BSS1 Protein Complex Regulates Plant Development via Brassinosteroid Signaling, The Plant Cell, vol. 27, Feb. 2015, pp. 375-390.
Wang et al., "Brassinosteroid Signaling Network and Regulation of Photomorphogenesis", The Annual Review of Genetics, 2012, 46, pp. 701-724.
Written Opinion of the International Searching Authority for PCT/JP2016/052052 (PCT/ISA/237) dated Apr. 12, 2016.

* cited by examiner

*Primary Examiner* — Eileen B O Hara
(74) *Attorney, Agent, or Firm* — Birch, Stewart, Kolasch & Birch LLP

(57) ABSTRACT

According to the present invention, a transgenic plant, wherein expression of the BSS1 gene having activity to bind to a BIL1 protein to inhibit the transfer of the BIL1 protein into the nucleus so as to down-regulate brassinosteroid signaling is suppressed or promoted, and a method for regulating plant growth, wherein expression of the BSS1 gene in a plant body is suppressed or promoted, are provided.

8 Claims, 15 Drawing Sheets

Specification includes a Sequence Listing.

Fig. 1
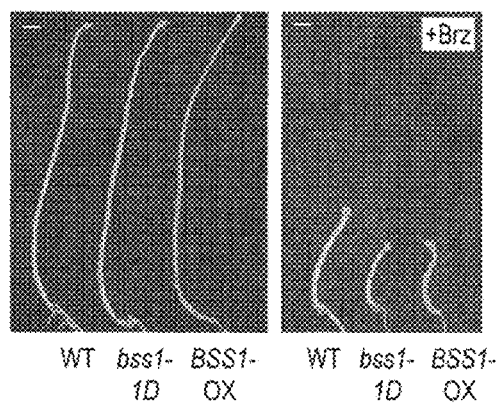
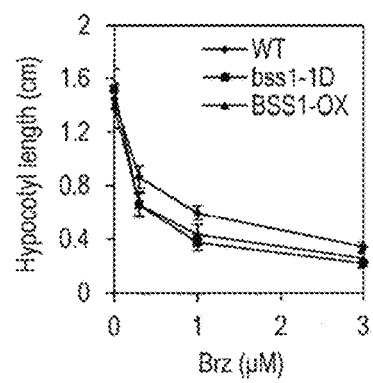
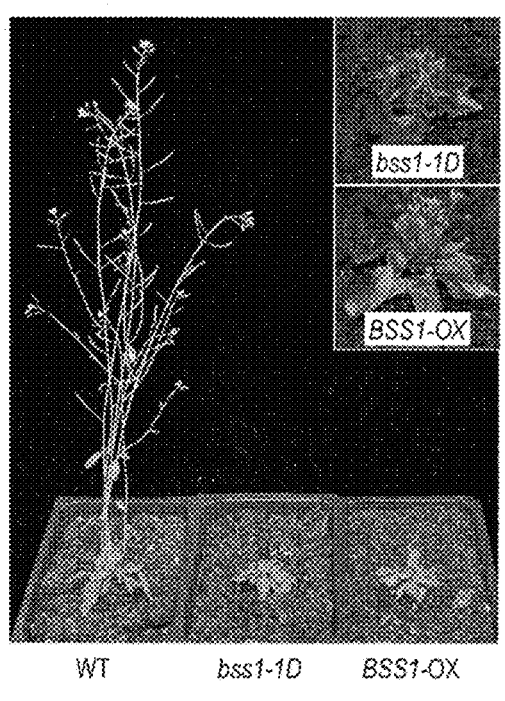
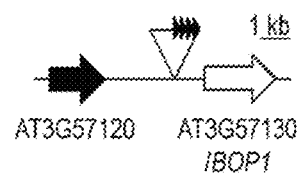
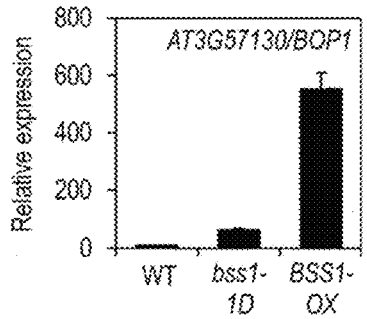

SEQUENCE LISTING

```
<160> NUMBER OF SEQ ID NOS: 34

<210> SEQ ID NO 1
<211> LENGTH: 861
<212> TYPE: DNA
<213> ORGANISM: Arabidopsis thaliana
<220> FEATURE:
<221> NAME/KEY: CDS
<222> LOCATION: (278)..(826)

<400> SEQUENCE: 1
cattcagatc tctgtctctt tctctcacta tatctatcta tctacccaca aaccaatctt      60
ctaaacacta tagtctctct ctctcttctt catcttctcc ataagcttct aaagatatat     120
aaaagcttgt gactcttctt cacttaaaga aatatttgct tacgaaagaa aaccctattc     180
tatatatcct acagcatact aaaatcaaag ggtacgacat ttttttcgtt cttttaaaac     240
cctaatttgt tgtatcaaag aaatcaacaa aggagct atg agc aat act ttc gaa      295
                                        Met Ser Asn Thr Phe Glu
                                         1               5 gaa tca ctc aaa tct atg tca ttg gat tac cta aac ctc tta atc aac       343
Glu Ser Leu Lys Ser Met Ser Leu Asp Tyr Leu Asn Leu Leu Ile Asn
             10                  15                  20 ggt caa gct ttc tcc gat gtc act ttc agc gtc gaa ggc cgt cta gtc       391
Gly Gln Ala Phe Ser Asp Val Thr Phe Ser Val Glu Gly Arg Leu Val
         25                  30                  35 cac gct cac cgt tgc atc ctc gct gct cgt agc ctc ttc ttc cgc aaa       439
His Ala His Arg Cys Ile Leu Ala Ala Arg Ser Leu Phe Phe Arg Lys
     40                  45                  50
```

| | | |
|---|---|---|
| ttc ttc tgt gaa tct gat cct tcg caa ccc gga gct gaa ccc gct aac<br>Phe Phe Cys Glu Ser Asp Pro Ser Gln Pro Gly Ala Glu Pro Ala Asn<br>55                         60                       65                     70 | | 487 |
| caa acc gga tca gga gcc aga gca gcc gca gta gga gtc ata ccg<br>Gln Thr Gly Ser Gly Ala Arg Ala Ala Ala Val Gly Gly Val Ile Pro<br>                    75                       80                     85 | | 535 |
| gtt aac tca gtc ggt tac gaa gtt ttc tta ctt cta ctt caa ttc ttg<br>Val Asn Ser Val Gly Tyr Glu Val Phe Leu Leu Leu Leu Gln Phe Leu<br>                    90                       95                    100 | | 583 |
| tac agt ggt caa gtc tca att gta cca cat aag cac gag cca aga tcg<br>Tyr Ser Gly Gln Val Ser Ile Val Pro His Lys His Glu Pro Arg Ser<br>                 105                    110                   115 | | 631 |
| aat tgt gga gat aga gga tgc tgg cac acg cat tgc act gca gcc gtc<br>Asn Cys Gly Asp Arg Gly Cys Trp His Thr His Cys Thr Ala Ala Val<br>        120                    125                    130 | | 679 |
| gat ctc tct tta gat att tta gcc gcc gct cgc tac ttt ggc gtc gag<br>Asp Leu Ser Leu Asp Ile Leu Ala Ala Ala Arg Tyr Phe Gly Val Glu<br>135                       140                    145                   150 | | 727 |
| cag ctc gcg ttg ctt act cag tgc aac ttt ctt tcc aga ttt aga cgg<br>Gln Leu Ala Leu Leu Thr Gln Cys Asn Phe Leu Ser Arg Phe Arg Arg<br>                 155                    160                   165 | | 775 |
| caa tgg act gat gtg ttt tgc aca ccg aga aat ttc ctt aaa atg gaa<br>Gln Trp Thr Asp Val Phe Cys Thr Pro Arg Asn Phe Leu Lys Met Glu<br>    170                    175                    180 | | 823 |
| tga tgcttttatt tttaatat acatactctt tattt | | 861 |

\<210\> SEQ ID NO 2
\<211\> LENGTH: 549
\<212\> TYPE: DNA
\<213\> ORGANISM: Arabidopsis thaliana

\<400\> SEQUENCE: 2

| | |
|---|---|
| atgagcaata ctttcgaaga atcactcaaa tctatgtcat tggattacct aaacctctta | 60 |
| atcaacggtc aagctttctc cgatgtcact ttcagcgtcg aaggccgtct agtccacgct | 120 |
| caccgttgca tcctcgctgc tcgtagcctc ttcttccgca aattcttctg tgaatctgat | 180 |
| ccttcgcaac ccggagctga acccgctaac caaaccggat caggagccag agcagccgca | 240 |
| gtaggaggag tcataccggt taactcagtc ggttacgaag ttttcttact tctacttcaa | 300 |
| ttcttgtaca gtggtcaagt ctcaattgta ccacataagc acgagccaag atcgaattgt | 360 |
| ggagatagag gatgctggca cacgcattgc actgcagccg tcgatctctc tttagatatt | 420 |
| ttagccgccg ctcgctactt tggcgtcgag cagctcgcgt tgcttactca gtgcaacttt | 480 |
| ctttccagat ttagacggca atggactgat gtgttttgca caccgagaaa tttccttaaa | 540 |
| atggaatga | 549 |

\<210\> SEQ ID NO 3
\<211\> LENGTH: 182
\<212\> TYPE: PRT
\<213\> ORGANISM: Arabidopsis thaliana

\<400\> SEQUENCE: 3

Met Ser Asn Thr Phe Glu Glu Ser Leu Lys Ser Met Ser Leu Asp Tyr
1                  5                    10                   15

Leu Asn Leu Leu Ile Asn Gly Gln Ala Phe Ser Asp Val Thr Phe Ser
              20                    25                    30

Val Glu Gly Arg Leu Val His Ala His Arg Cys Ile Leu Ala Ala Arg
        35                    40                    45

```
Ser Leu Phe Phe Arg Lys Phe Phe Cys Glu Ser Asp Pro Ser Gln Pro
 50                  55                  60

Gly Ala Glu Pro Ala Asn Gln Thr Gly Ser Gly Ala Arg Ala Ala
 65                  70                  75                  80

Val Gly Gly Val Ile Pro Val Asn Ser Val Gly Tyr Glu Val Phe Leu
                     85                  90                  95

Leu Leu Leu Gln Phe Leu Tyr Ser Gly Gln Val Ser Ile Val Pro His
                100                 105                 110

Lys His Glu Pro Arg Ser Asn Cys Gly Asp Arg Gly Cys Trp His Thr
                115                 120                 125

His Cys Thr Ala Ala Val Asp Leu Ser Leu Asp Ile Leu Ala Ala Ala
                130                 135                 140

Arg Tyr Phe Gly Val Glu Gln Leu Ala Leu Leu Thr Gln Cys Asn Phe
145                 150                 155                 160

Leu Ser Arg Phe Arg Arg Gln Trp Thr Asp Val Phe Cys Thr Pro Arg
                165                 170                 175

Asn Phe Leu Lys Met Glu
                180

<210> SEQ ID NO 4
<211> LENGTH: 2453
<212> TYPE: DNA
<213> ORGANISM: Oryza sativa
<220> FEATURE:
<221> NAME/KEY: CDS
<222> LOCATION: (1)..(528)
<220> FEATURE:
<221> NAME/KEY: CDS
<222> LOCATION: (1497)..(2453)

<400> SEQUENCE: 4 atg agc tcc gag gac tcg ctc aaa tcc ttg tcg ctt gac tac ctc agc        48
Met Ser Ser Glu Asp Ser Leu Lys Ser Leu Ser Leu Asp Tyr Leu Ser
 1               5                  10                  15 ctg ctc atc aat ggc cag gcc ttc agc gac gtc gcc ttc agc gtc gag        96
Leu Leu Ile Asn Gly Gln Ala Phe Ser Asp Val Ala Phe Ser Val Glu
                 20                  25                  30 ggc cgc ctc gtg cac gcc cac cgc tgc gtg ctg gcg gcg cgg agc ttg       144
Gly Arg Leu Val His Ala His Arg Cys Val Leu Ala Ala Arg Ser Leu
             35                  40                  45 ttc ttc agg aag ttg ttc tgc ggg ctc gat ccg aat cac cag ccg ccg       192
Phe Phe Arg Lys Leu Phe Cys Gly Leu Asp Pro Asn His Gln Pro Pro
 50                  55                  60 ccg cca ccg ccg ccg tta aac tgg ccg atg gcg ggg gga ggc ggc ggc       240
Pro Pro Pro Pro Pro Leu Asn Trp Pro Met Ala Gly Gly Gly Gly Gly
 65                  70                  75                  80 ggc tct ggt ggt gga ggg cgt ggc ggc gcc ggt ggt ggt gga gga gcg       288
Gly Ser Gly Gly Gly Gly Arg Gly Gly Ala Gly Gly Gly Gly Gly Ala
                 85                  90                  95 cct gcc acg ccg gag ctt gtc atc ccc gtc agc tcg atc cgg tac gag       336
Pro Ala Thr Pro Glu Leu Val Ile Pro Val Ser Ser Ile Arg Tyr Glu
             100                 105                 110 gtg ctc gtg ctc gtg ctg cag ttc ctg tac agc ggg cag gcg tcg gtg       384
Val Leu Val Leu Val Leu Gln Phe Leu Tyr Ser Gly Gln Ala Ser Val
         115                 120                 125 gcg gcg ccc aag agc ggg ccg ctc ccg ggg tgc ggc gcc cgg ggt tgc       432
Ala Ala Pro Lys Ser Gly Pro Leu Pro Gly Cys Gly Ala Arg Gly Cys
     130                 135                 140 tgg cac acg cgg tgc ggc gcc gcc gtc gac ctc gcc ctc gac acg ctc       480
Trp His Thr Arg Cys Gly Ala Ala Val Asp Leu Ala Leu Asp Thr Leu
```

```
Trp His Thr Arg Cys Gly Ala Ala Val Asp Leu Ala Leu Asp Thr Leu
145                 150                 155                 160 gcc gct gcg cgc tcc ttc ggc gtc gag cag ctc gcc ctg ctg gtt cag      528
Ala Ala Ala Arg Ser Phe Gly Val Glu Gln Leu Ala Leu Leu Val Gln
                165                 170                 175 gtactgcgcg aaaattcag gaacacgacg tagtatatac gcgtcatgca tcctgcagct      588
gcaaataatt tgaaattcct cttccatgtg cttgcaattc gatcttggga tctgctgcta     648
acactgggta ttgattaaga gtacatgatg gtagttaggc tggcatgatt ggagcatctt     708
tttggtgaca ttaaggagtc agcagaagca atgttcaagt ctgagctgat cctgctgcat     768
gcttgcctag atccctaggt tgcatgcccc ctttgccttt ttttccgatt actgagcgag     828
ctgagctgca cgattcatgc actactgctc tcaactgtgg catctgatcc atgcgcagta     888
gctgcagcag aatctagtgc atgccctcac ttcattcatc gcaatttttt aacattttt      948 cttgtgttct ttttttttc gggagtgaga tagatggggt atagtgtact aataggactg     1008
agtcgtctct agtctcgatt gcttttctgc tgcttcgccc ttgctgcttc tgtcatcact     1068
tgtcatggag cttctaactc atctttacta ggaagggtct tttcaagctc ttgttgtgtc     1128
tgtcccttcc ttacatcaca tccatcccca tgcttgcttt cctgatttct taattcgcat     1188
catttcggca tttccattgc tagggtttct tggagatcca acccggggtg gccacttcga     1248
tcctaactag catcatttcc aaaaataatt cttagtgtac agcatgcatg ctgtgttcta     1308
agcaaagtac agttaagctc atcatacatt tttgcatatc tctctgaaca gaactgaaga     1368
aagtactact actacatgct aagaacaaca tttcatgctg ctaattagct gtcgtgcatt     1428
tgagggtgat taattaagca tcttaattga actaatggcg agttgcacaa tgcaatgtgt     1488 taatgcag aag cag ctg gag agc atg gtg aag gag gcg tcg gtg gac gac    1538
         Lys Gln Leu Glu Ser Met Val Lys Glu Ala Ser Val Asp Asp
                 180                 185                 190 gtg atg aag gtg ctg atg gcg tcg cgc aag ttc gag atg cag gag ctg      1586
Val Met Lys Val Leu Met Ala Ser Arg Lys Phe Glu Met Gln Glu Leu
                195                 200                 205 tgg gcg act tgc tcc cac ctc gtc gcg cgc tcc ggc ctc tcc gcc gat      1634
Trp Ala Thr Cys Ser His Leu Val Ala Arg Ser Gly Leu Ser Ala Asp
            210                 215                 220 ctc ctc gcc aag cac ctc ccc atc gat gtg gtc gcc aag atc gag gag      1682
Leu Leu Ala Lys His Leu Pro Ile Asp Val Val Ala Lys Ile Glu Glu
            225                 230                 235 atc cgc gcc aag tcg ccg ctc gcc gcg gtg gcc gcg ccg cgc tcg ccg      1730
Ile Arg Ala Lys Ser Pro Leu Ala Ala Val Ala Ala Pro Arg Ser Pro
        240                 245                 250 ttc ctg acg cac cac tac ctc ccc atg aac ccg gcg tcc tcc gcg gcg      1778
Phe Leu Thr His His Tyr Leu Pro Met Asn Pro Ala Ser Ser Ala Ala
255                 260                 265                 270 gac cgc gac aac aag atc cgg cgc atg cgg cgc gcc ctc gac gcc gcc      1826
Asp Arg Asp Asn Lys Ile Arg Arg Met Arg Arg Ala Leu Asp Ala Ala
                275                 280                 285 gac atc gag ctc gtc aaa ctg atg gtc atg ggc gag ggc ctg gac ctc      1874
Asp Ile Glu Leu Val Lys Leu Met Val Met Gly Glu Gly Leu Asp Leu
                290                 295                 300 gac gac gcg ctc gcc gtc cac tac gcc gtg cag cac tgc aac cgc gac      1922
Asp Asp Ala Leu Ala Val His Tyr Ala Val Gln His Cys Asn Arg Asp
            305                 310                 315 gtc gtc aag gcg ctg ctc gag ctc ggc gcc gcc gac gtc aac tcc cgc      1970
Val Val Lys Ala Leu Leu Glu Leu Gly Ala Ala Asp Val Asn Ser Arg
        320                 325                 330
```

| | | | | | | | | | | | | | | | | |
|---|---|---|---|---|---|---|---|---|---|---|---|---|---|---|---|---|
|gcc|ggc|ccg|aca|ggc|aaa|acc|gcc|ctg|cac|ctg|gcg|gcg|gag|atg|gtc|2018|
|Ala|Gly|Pro|Thr|Gly|Lys|Thr|Ala|Leu|His|Leu|Ala|Ala|Glu|Met|Val| |
|335| | | |340| | | |345| | | |350| | | | |

```
gcc ggc ccg aca ggc aaa acc gcc ctg cac ctg gcg gcg gag atg gtc      2018
Ala Gly Pro Thr Gly Lys Thr Ala Leu His Leu Ala Ala Glu Met Val
335                 340                 345                 350 tcc ccg gac atg gtg tcc gtg ctg ctc gac cac cac gcc gac ccg aac      2066
Ser Pro Asp Met Val Ser Val Leu Leu Asp His His Ala Asp Pro Asn
                355                 360                 365 tcc agg acg ctc gac ggc gtc acg ccg ctc gac gtg ctc cgc agc ctc      2114
Ser Arg Thr Leu Asp Gly Val Thr Pro Leu Asp Val Leu Arg Ser Leu
            370                 375                 380 acc tcc gag ttc ctc ttc aag ggc gcc gtg ccg ggg ctg acg cac atc      2162
Thr Ser Glu Phe Leu Phe Lys Gly Ala Val Pro Gly Leu Thr His Ile
        385                 390                 395 gag ccc aac aag ctc agg ctc tgc ctc gag ctc gtg cag tcg gcg gtg      2210
Glu Pro Asn Lys Leu Arg Leu Cys Leu Glu Leu Val Gln Ser Ala Val
    400                 405                 410 atg gtg acc acg cgt gac gac ggc gcg cct gtc acc ggc ggc gcc gag      2258
Met Val Thr Thr Arg Asp Asp Gly Ala Pro Val Thr Gly Gly Ala Glu
415                 420                 425                 430 gcc ggc gga agc gac ggc ggc aac ttc ccg agg agc gac gcc gac gac      2306
Ala Gly Gly Ser Asp Gly Gly Asn Phe Pro Arg Ser Asp Ala Asp Asp
                435                 440                 445 agc ttg gtg agc ctg acg atg aac tcg acg ctc atg tac cag ggc cag      2354
Ser Leu Val Ser Leu Thr Met Asn Ser Thr Leu Met Tyr Gln Gly Gln
            450                 455                 460 gaa atg gcg gcg gcc gtg gcc gcc ggc gag ggg agg aaa agc aat aac      2402
Glu Met Ala Ala Ala Val Ala Ala Gly Glu Gly Arg Lys Ser Asn Asn
        465                 470                 475 ggc cga ggg agc ccg ccg ccc gcc atg tac ttc ccc aat ggc ttc gca      2450
Gly Arg Gly Ser Pro Pro Pro Ala Met Tyr Phe Pro Asn Gly Phe Ala
    480                 485                 490 taa                                                                   2453

<210> SEQ ID NO 5
<211> LENGTH: 1485
<212> TYPE: DNA
<213> ORGANISM: Oryza sativa

<400> SEQUENCE: 5
atgagctccg aggactcgct caaatccttg tcgcttgact acctcagcct gctcatcaat      60
ggccaggcct tcagcgacgt cgccttcagc gtcgagggcc gcctcgtgca cgcccaccgc     120
tgcgtgctgg cggcgcggag cttgttcttc aggaagttgt tctgcgggct cgatccgaat     180
caccagccgc cgccgccacc gccgccgtta aactggccga tggcgggggg aggcggcggc     240
ggctctggtg gtggagggcg tggcggcgcc ggtggtggtg gaggagcgcc tgccacgccg     300
gagcttgtca tccccgtcag ctcgatccgg tacgaggtgc tcgtgctcgt gctgcagttc     360
ctgtacagcg ggcaggcgtc ggtggcggcg cccaagagcg ggccgctccc ggggtgcggc     420 gcccgggggtt gctggcacac gcggtgcggc gccgccgtcg acctcgccct cgacacgctc     480
gccgctgcgc gctccttcgg cgtcgagcag ctcgccctgc tggttcagaa gcagctggag     540
agcatggtga aggaggcgtc ggtggacgac gtgatgaagg tgctgatggc gtcgcgcaag     600
ttcgagatgc aggagctgtg ggcgacttgc tcccacctcg tcgcgcgctc cggcctctcc     660
gccgatctcc tcgccaagca cctccccatc gatgtggtcg ccaagatcga ggagatccgc     720
gccaagtcgc cgctcgccgc ggtggccgcg ccgcgctcgc cgttcctgac gcaccactac     780
ctccccatga accggcgtc ctccgcggcg gaccgcgaca acaagatccg gcgcatgcgg     840
cgcgccctcg acgccgccga catcgagctc gtcaaactga tggtcatggg cgagggcctg     900
```

```
gacctcgacg acgcgctcgc cgtccactac gccgtgcagc actgcaaccg cgacgtcgtc      960
aaggcgctgc tcgagctcgg cgccgccgac gtcaactccc gcgccggccc gacaggcaaa     1020
accgccctgc acctggcggc ggagatggtc tccccggaca tggtgtccgt gctgctcgac     1080
caccacgccg acccgaactc caggacgctc gacggcgtca cgccgctcga cgtgctccgc     1140
agcctcacct ccgagttcct cttcaagggc gccgtgccgg ggctgacgca catcgagccc     1200
aacaagctca ggtctctgcct cgagctcgtg cagtcggcgg tgatggtgac cacgcgtgac     1260
gacggcgcgc tgtcaccgg cggcgccgag gccggcggaa gcgacggcgg caacttcccg     1320
aggagcgacg ccgacgacag cttggtgagc ctgacgatga actcgacgct catgtaccag     1380
ggccaggaaa tggcggcggc cgtggccgcc ggcgagggga ggaaaagcaa taacggccga     1440 gggagccccgc cgcccgccat gtacttcccc aatggcttcg cataa                    1485
```

<210> SEQ ID NO 6
<211> LENGTH: 494
<212> TYPE: PRT
<213> ORGANISM: Oryza sativa

<400> SEQUENCE: 6

```
Met Ser Ser Glu Asp Ser Leu Lys Ser Leu Ser Leu Asp Tyr Leu Ser
1               5                   10                  15

Leu Leu Ile Asn Gly Gln Ala Phe Ser Asp Val Ala Phe Ser Val Glu
            20                  25                  30

Gly Arg Leu Val His Ala His Arg Cys Val Leu Ala Ala Arg Ser Leu
        35                  40                  45

Phe Phe Arg Lys Leu Phe Cys Gly Leu Asp Pro Asn His Gln Pro Pro
    50                  55                  60

Pro Pro Pro Pro Leu Asn Trp Pro Met Ala Gly Gly Gly Gly Gly Gly
65                  70                  75                  80

Gly Ser Gly Gly Gly Arg Gly Gly Ala Gly Gly Gly Gly Ala
            85                  90                  95

Pro Ala Thr Pro Glu Leu Val Ile Pro Val Ser Ser Ile Arg Tyr Glu
            100                 105                 110

Val Leu Val Leu Val Leu Gln Phe Leu Tyr Ser Gly Gln Ala Ser Val
        115                 120                 125

Ala Ala Pro Lys Ser Gly Pro Leu Pro Gly Cys Gly Ala Arg Gly Cys
    130                 135                 140

Trp His Thr Arg Cys Gly Ala Ala Val Asp Leu Ala Leu Asp Thr Leu
145                 150                 155                 160

Ala Ala Ala Arg Ser Phe Gly Val Glu Gln Leu Ala Leu Leu Val Gln
                165                 170                 175

Lys Gln Leu Glu Ser Met Val Lys Glu Ala Ser Val Asp Asp Val Met
            180                 185                 190

Lys Val Leu Met Ala Ser Arg Lys Phe Glu Met Gln Glu Leu Trp Ala
        195                 200                 205

Thr Cys Ser His Leu Val Ala Arg Ser Gly Leu Ser Ala Asp Leu Leu
    210                 215                 220

Ala Lys His Leu Pro Ile Asp Val Val Ala Lys Ile Glu Glu Ile Arg
225                 230                 235                 240

Ala Lys Ser Pro Leu Ala Ala Val Ala Ala Pro Arg Ser Pro Phe Leu
                245                 250                 255

Thr His His Tyr Leu Pro Met Asn Pro Ala Ser Ser Ala Ala Asp Arg
            260                 265                 270
```

Asp Asn Lys Ile Arg Arg Met Arg Arg Ala Leu Asp Ala Ala Asp Ile
            275                 280                 285

Glu Leu Val Lys Leu Met Val Met Gly Glu Gly Leu Asp Leu Asp Asp
        290                 295                 300

Ala Leu Ala Val His Tyr Ala Val Gln His Cys Asn Arg Asp Val Val
305                 310                 315                 320

Lys Ala Leu Leu Glu Leu Gly Ala Ala Asp Val Asn Ser Arg Ala Gly
                325                 330                 335

Pro Thr Gly Lys Thr Ala Leu His Leu Ala Ala Glu Met Val Ser Pro
            340                 345                 350

Asp Met Val Ser Val Leu Leu Asp His His Ala Asp Pro Asn Ser Arg
        355                 360                 365

Thr Leu Asp Gly Val Thr Pro Leu Asp Val Leu Arg Ser Leu Thr Ser
370                 375                 380

Glu Phe Leu Phe Lys Gly Ala Val Pro Gly Leu Thr His Ile Glu Pro
385                 390                 395                 400

Asn Lys Leu Arg Leu Cys Leu Glu Leu Val Gln Ser Ala Val Met Val
                405                 410                 415

Thr Thr Arg Asp Asp Gly Ala Pro Val Thr Gly Gly Ala Glu Ala Gly
            420                 425                 430

Gly Ser Asp Gly Gly Asn Phe Pro Arg Ser Asp Ala Asp Asp Ser Leu
        435                 440                 445

Val Ser Leu Thr Met Asn Ser Thr Leu Met Tyr Gln Gly Gln Glu Met
450                 455                 460

Ala Ala Ala Val Ala Ala Gly Glu Gly Arg Lys Ser Asn Asn Gly Arg
465                 470                 475                 480

Gly Ser Pro Pro Pro Ala Met Tyr Phe Pro Asn Gly Phe Ala
                485                 490

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
catgacctaa cctcgacttt                                              20

<210> SEQ ID NO 8
<211> LENGTH: 18
<212> TYPE: DNA
<213> ORGANISM: Artificial Sequence
<220> FEATURE:
<223> OTHER INFORMATION: primer

<400> SEQUENCE: 8
cccatcacca ttagcttc                                                18

<210> SEQ ID NO 9
<211> LENGTH: 19
<212> TYPE: DNA
<213> ORGANISM: Artificial Sequence
<220> FEATURE:
<223> OTHER INFORMATION: primer

<400> SEQUENCE: 9
cgccatccaa gctgttctc                                               19

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tcacgtccag caaggtcaag                                            20

<210> SEQ ID NO 11
<211> LENGTH: 33
<212> TYPE: DNA
<213> ORGANISM: Artificial Sequence
<220> FEATURE:
<223> OTHER INFORMATION: primer

<400> SEQUENCE: 11
caccatgagc aatacttcga agaatcactc aaa                             33

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
gaaatggtgg tggtggtgat gatacatc                                   28

<210> SEQ ID NO 13
<211> LENGTH: 33
<212> TYPE: DNA
<213> ORGANISM: Artificial Sequence
<220> FEATURE:
<223> OTHER INFORMATION: primer

<400> SEQUENCE: 13
caccatatgg tcgatcccaa accaacagga gaa                             33

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
agtaagcaac gcgagctgct cgacgccaaa gta                             33

<210> SEQ ID NO 15
<211> LENGTH: 33
<212> TYPE: DNA
<213> ORGANISM: Artificial Sequence
<220> FEATURE:
<223> OTHER INFORMATION: primer

<400> SEQUENCE: 15
caccatatgg tcgatcccaa accaacagga gaa                             33

<210> SEQ ID NO 16
<211> LENGTH: 28
<212> TYPE: DNA
<213> ORGANISM: Artificial Sequence
<220> FEATURE:
<223> OTHER INFORMATION: primer

<400> SEQUENCE: 16
gaaatggtgg tggtggtgat gatacatc                                              28

<210> SEQ ID NO 17
<211> LENGTH: 24
<212> TYPE: DNA
<213> ORGANISM: Artificial Sequence
<220> FEATURE:
<223> OTHER INFORMATION: primer

<400> SEQUENCE: 17
caccatgact tcggatggag ctac                                                  24

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
accacgagcc ttcccatttc c                                                     21

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
cgagtcttgg aacgctgat                                                        19

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
cttcttgttg aaagccacgg                                                       20

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
gccaaattga cactcgctgt aa                                                    22

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
gacggtaggt gcatgctgat aa                                                    22

<210> SEQ ID NO 23

```
<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
gaaggactcg ggcttgagat                                                   20

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
gacgccgctt tcacattg                                                     18

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gagatatgtg gtgccggttt                                                   20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gtattgttaa gccgcccatt                                                   20

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
ctagaaatgg tggtggtggt gatgatac                                          28

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
caccatgacg tctgacggag caac                                              24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
```

```
actatgagct ttaccatttc caag                                          24
```

<210> SEQ ID NO 30
<211> LENGTH: 37
<212> TYPE: DNA
<213> ORGANISM: Artificial Sequence
<220> FEATURE:
<223> OTHER INFORMATION: primer

<400> SEQUENCE: 30

```
caccatgagc tccgaggact cgctcaaatc cttgtcg                            37
```

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31

```
ttatgcgaag ccattgggga agtacatggc ggg                                33
```

<210> SEQ ID NO 32
<211> LENGTH: 467
<212> TYPE: PRT
<213> ORGANISM: Arabidopsis thaliana
<220> FEATURE:
<221> NAME/KEY: misc_feature
<223> OTHER INFORMATION: BSS1/BOP1

<400> SEQUENCE: 32

```
Met Ser Asn Thr Phe Glu Glu Ser Leu Lys Ser Met Ser Leu Asp Tyr
1               5                   10                  15

Leu Asn Leu Leu Ile Asn Gly Gln Ala Phe Ser Asp Val Thr Phe Ser
            20                  25                  30

Val Glu Gly Arg Leu Val His Ala His Arg Cys Ile Leu Ala Ala Arg
        35                  40                  45

Ser Leu Phe Phe Arg Lys Phe Phe Cys Glu Ser Asp Pro Ser Gln Pro
    50                  55                  60

Gly Ala Glu Pro Ala Asn Gln Thr Gly Ser Gly Ala Arg Ala Ala Ala
65                  70                  75                  80

Val Gly Gly Val Ile Pro Val Asn Ser Val Gly Tyr Glu Val Phe Leu
                85                  90                  95

Leu Leu Leu Gln Phe Leu Tyr Ser Gly Gln Val Ser Ile Val Pro His
            100                 105                 110

Lys His Glu Pro Arg Ser Asn Cys Gly Asp Arg Gly Cys Trp His Thr
        115                 120                 125

His Cys Thr Ala Ala Val Asp Leu Ser Leu Asp Ile Leu Ala Ala Ala
    130                 135                 140

Arg Tyr Phe Gly Val Glu Gln Leu Ala Leu Leu Thr Gln Lys His Leu
145                 150                 155                 160

Thr Ser Met Val Glu Lys Ala Ser Ile Glu Asp Val Met Lys Val Leu
                165                 170                 175

Ile Ala Ser Arg Lys Gln Asp Met His Gln Leu Trp Thr Thr Cys Ser
            180                 185                 190

Tyr Leu Ile Ala Lys Ser Gly Leu Pro Gln Glu Ile Leu Ala Lys His
        195                 200                 205

Leu Pro Ile Glu Leu Val Ala Lys Ile Glu Glu Leu Arg Leu Lys Ser
    210                 215                 220
```

```
Ser Met Pro Leu Arg Ser Leu Met Pro His His Asp Leu Thr Ser
225                 230                 235                 240

Thr Leu Asp Leu Glu Asp Gln Lys Ile Arg Met Arg Arg Ala Leu
            245                 250                 255

Asp Ser Ser Asp Val Glu Leu Val Lys Leu Met Val Met Gly Glu Gly
        260                 265                 270

Leu Asn Leu Asp Glu Ser Leu Ala Leu Ile Tyr Ala Val Glu Asn Cys
    275                 280                 285

Ser Arg Glu Val Val Lys Ala Leu Leu Glu Leu Gly Ala Ala Asp Val
290                 295                 300

Asn Tyr Pro Ala Gly Pro Thr Gly Lys Thr Ala Leu His Ile Ala Ala
305                 310                 315                 320

Glu Met Val Ser Pro Asp Met Val Ala Val Leu Leu Asp His His Ala
                325                 330                 335

Asp Pro Asn Val Gln Thr Val Asp Gly Ile Thr Pro Leu Asp Ile Leu
            340                 345                 350

Arg Thr Leu Thr Ser Asp Phe Leu Phe Lys Gly Ala Ile Pro Gly Leu
        355                 360                 365

Thr His Ile Glu Pro Asn Lys Leu Arg Leu Cys Leu Glu Leu Val Gln
370                 375                 380

Ser Ala Ala Leu Val Ile Ser Arg Glu Glu Gly Asn Asn Ser Asn
385                 390                 395                 400

Asp Asn Asn Thr Met Ile Tyr Pro Arg Met Lys Asp Glu His Thr Ser
                405                 410                 415

Gly Ser Ser Leu Asp Ser Arg Leu Val Tyr Leu Asn Leu Gly Ala Thr
            420                 425                 430

Asn Arg Asp Ile Gly Asp Asp Asn Ser Asn Gln Arg Glu Gly Met Asn
        435                 440                 445

Leu His His His His Asp Pro Ser Thr Met Tyr His His His His
    450                 455                 460

His His Phe
465

<210> SEQ ID NO 33
<211> LENGTH: 491
<212> TYPE: PRT
<213> ORGANISM: Arabidopsis thaliana
<220> FEATURE:
<221> NAME/KEY: misc_feature
<223> OTHER INFORMATION: BOP2

<400> SEQUENCE: 33

Met Ser Asn Leu Glu Glu Ser Leu Arg Ser Leu Ser Leu Asp Phe Leu
1               5                   10                  15

Asn Leu Leu Ile Asn Gly Gln Ala Phe Ser Asp Val Thr Phe Ser Val
            20                  25                  30

Glu Gly Arg Leu Val His Ala His Arg Cys Ile Leu Ala Ala Arg Ser
        35                  40                  45

Leu Phe Phe Arg Lys Phe Phe Cys Gly Thr Asp Ser Pro Gln Pro Val
    50                  55                  60

Thr Gly Ile Asp Pro Thr Gln His Gly Ser Val Pro Ala Ser Pro Thr
65                  70                  75                  80

Arg Gly Ser Thr Ala Pro Ala Gly Ile Ile Pro Val Asn Ser Val Gly
                85                  90                  95

Tyr Glu Val Phe Leu Leu Leu Leu Gln Phe Leu Tyr Ser Gly Gln Val
```

```
            100               105                110
Ser Ile Val Pro Gln Lys His Glu Pro Arg Pro Asn Cys Gly Glu Arg
            115               120                125
Gly Cys Trp His Thr His Cys Ser Ala Ala Val Asp Leu Ala Leu Asp
            130               135            140
Thr Leu Ala Ala Ser Arg Tyr Phe Gly Val Glu Gln Leu Ala Leu Leu
145             150              155                 160
Thr Gln Lys Gln Leu Ala Ser Met Val Glu Lys Ala Ser Ile Glu Asp
                165              170              175
Val Met Lys Val Leu Ile Ala Ser Arg Lys Gln Asp Met His Gln Leu
            180              185              190
Trp Thr Thr Cys Ser His Leu Val Ala Lys Ser Gly Leu Pro Pro Glu
            195              200              205
Ile Leu Ala Lys His Leu Pro Ile Asp Val Val Thr Lys Ile Glu Glu
            210              215              220
Leu Arg Leu Lys Ser Ser Ile Ala Arg Arg Ser Leu Met Pro His Asn
225             230              235              240
His His His Asp Leu Ser Val Ala Gln Asp Leu Glu Asp Gln Lys Ile
                245              250              255
Arg Arg Met Arg Arg Ala Leu Asp Ser Ser Asp Val Glu Leu Val Lys
            260              265              270
Leu Met Val Met Gly Glu Gly Leu Asn Leu Asp Glu Ser Leu Ala Leu
            275              280              285
His Tyr Ala Val Glu Ser Cys Ser Arg Glu Val Val Lys Ala Leu Leu
            290              295              300
Glu Leu Gly Ala Ala Asp Val Asn Tyr Pro Ala Gly Pro Ala Gly Lys
305             310              315                 320
Thr Pro Leu His Ile Ala Ala Glu Met Val Ser Pro Asp Met Val Ala
                325              330              335
Val Leu Leu Asp His His Ala Asp Pro Asn Val Arg Thr Val Gly Gly
                340              345              350
Ile Thr Pro Leu Asp Ile Leu Arg Thr Leu Thr Ser Asp Phe Leu Phe
            355              360              365
Lys Gly Ala Val Pro Gly Leu Thr His Ile Glu Pro Asn Lys Leu Arg
            370              375              380
Leu Cys Leu Glu Leu Val Gln Ser Ala Ala Met Val Ile Ser Arg Glu
385             390              395                 400
Glu Gly Asn Asn Ser Asn Asn Gln Asn Asn Asp Asn Asn Thr Gly Ile
                405              410              415
Tyr Pro His Met Asn Glu Glu His Asn Ser Gly Ser Ser Gly Gly Ser
                420              425              430
Asn Asn Asn Leu Asp Ser Arg Leu Val Tyr Leu Asn Leu Gly Ala Gly
            435              440              445
Thr Gly Gln Met Gly Pro Gly Arg Asp Gln Gly Asp Asp His Asn Ser
            450              455              460
Gln Arg Glu Gly Met Ser Arg His His His His Gln Asp Pro Ser
465             470              475              480
Thr Met Tyr His His His Gln His His Phe
                485              490

<210> SEQ ID NO 34
<211> LENGTH: 593
<212> TYPE: PRT
<213> ORGANISM: Arabidopsis thaliana
```

<220> FEATURE:
<221> NAME/KEY: misc_feature
<223> OTHER INFORMATION: NPR1

<400> SEQUENCE: 34

Met Asp Thr Thr Ile Asp Gly Phe Ala Asp Ser Tyr Glu Ile Ser Ser
1               5                   10                  15

Thr Ser Phe Val Ala Thr Asp Asn Thr Asp Ser Ser Ile Val Tyr Leu
            20                  25                  30

Ala Ala Glu Gln Val Leu Thr Gly Pro Asp Val Ser Ala Leu Gln Leu
        35                  40                  45

Leu Ser Asn Ser Phe Glu Ser Val Phe Asp Ser Pro Asp Asp Phe Tyr
    50                  55                  60

Ser Asp Ala Lys Leu Val Leu Ser Asp Gly Arg Glu Val Ser Phe His
65                  70                  75                  80

Arg Cys Val Leu Ser Ala Arg Ser Ser Phe Phe Lys Ser Ala Leu Ala
                85                  90                  95

Ala Ala Lys Lys Glu Lys Asp Ser Asn Asn Thr Ala Ala Val Lys Leu
            100                 105                 110

Glu Leu Lys Glu Ile Ala Lys Asp Tyr Glu Val Gly Phe Asp Ser Val
        115                 120                 125

Val Thr Val Leu Ala Tyr Val Tyr Ser Ser Arg Val Arg Pro Pro Pro
    130                 135                 140

Lys Gly Val Ser Glu Cys Ala Asp Glu Asn Cys Cys His Val Ala Cys
145                 150                 155                 160

Arg Pro Ala Val Asp Phe Met Leu Glu Val Leu Tyr Leu Ala Phe Ile
                165                 170                 175

Phe Lys Ile Pro Glu Leu Ile Thr Leu Tyr Gln Arg His Leu Leu Asp
            180                 185                 190

Val Val Asp Lys Val Val Ile Glu Asp Thr Leu Val Ile Leu Lys Leu
        195                 200                 205

Ala Asn Ile Cys Gly Lys Ala Cys Met Lys Leu Leu Asp Arg Cys Lys
    210                 215                 220

Glu Ile Ile Val Lys Ser Asn Val Asp Met Val Ser Leu Glu Lys Ser
225                 230                 235                 240

Leu Pro Glu Glu Leu Val Lys Glu Ile Ile Asp Arg Arg Lys Glu Leu
                245                 250                 255

Gly Leu Glu Val Pro Lys Val Lys Lys His Val Ser Asn Val His Lys
            260                 265                 270

Ala Leu Asp Ser Asp Asp Ile Glu Leu Val Lys Leu Leu Leu Lys Glu
        275                 280                 285

Asp His Thr Asn Leu Asp Asp Ala Cys Ala Leu His Phe Ala Val Ala
    290                 295                 300

Tyr Cys Asn Val Lys Thr Ala Thr Asp Leu Leu Lys Leu Asp Leu Ala
305                 310                 315                 320

Asp Val Asn His Arg Asn Pro Arg Gly Tyr Thr Val Leu His Val Ala
                325                 330                 335

Ala Met Arg Lys Glu Pro Gln Leu Ile Leu Ser Leu Leu Glu Lys Gly
            340                 345                 350

Ala Ser Ala Ser Glu Ala Thr Leu Glu Gly Arg Thr Ala Leu Met Ile
        355                 360                 365

Ala Lys Gln Ala Thr Met Ala Val Glu Cys Asn Asn Ile Pro Glu Gln
    370                 375                 380

Cys Lys His Ser Leu Lys Gly Arg Leu Cys Val Glu Ile Leu Glu Gln

-continued

```
385             390             395             400
Glu Asp Lys Arg Glu Gln Ile Pro Arg Asp Val Pro Pro Ser Phe Ala
            405             410             415

Val Ala Ala Asp Glu Leu Lys Met Thr Leu Leu Asp Leu Glu Asn Arg
            420             425             430

Val Ala Leu Ala Gln Arg Leu Phe Pro Thr Glu Ala Gln Ala Ala Met
            435             440             445

Glu Ile Ala Glu Met Lys Gly Thr Cys Glu Phe Ile Val Thr Ser Leu
    450             455             460

Glu Pro Asp Arg Leu Thr Gly Thr Lys Arg Thr Ser Pro Gly Val Lys
465             470             475             480

Ile Ala Pro Phe Arg Ile Leu Glu Glu His Gln Ser Arg Leu Lys Ala
            485             490             495

Leu Ser Lys Thr Val Glu Leu Gly Lys Arg Phe Phe Pro Arg Cys Ser
            500             505             510

Ala Val Leu Asp Gln Ile Met Asn Cys Glu Asp Leu Thr Gln Leu Ala
            515             520             525

Cys Gly Glu Asp Asp Thr Ala Glu Lys Arg Leu Gln Lys Lys Gln Arg
    530             535             540

Tyr Met Glu Ile Gln Glu Thr Leu Lys Lys Ala Phe Ser Glu Asp Asn
545             550             555             560

Leu Glu Leu Gly Asn Ser Ser Leu Thr Asp Ser Thr Ser Ser Thr Ser
            565             570             575

Lys Ser Thr Gly Gly Lys Arg Ser Asn Arg Lys Leu Ser His Arg Arg
            580             585             590

Arg
```

METHOD FOR REGULATING PLANT GROWTH

REFERENCE TO SEQUENCE LISTING SUBMITTED VIA EFS-WEB

This application includes an electronically submitted sequence listing in .txt format. The .txt file contains a sequence listing entitled "2018-03-23 SequenceListing 1254-0571PUS2" created on Mar. 20, 2018 and is 39,047 bytes in size. The sequence listing contained in this .txt file is part of the specification and is hereby incorporated by reference herein in its entirety.

TECHNICAL FIELD

The present invention relates to the use of the BSS gene that down-regulates brassinosteroid signaling.

BACKGROUND ART

Plant hormones are chemicals that are present in the living body of a plant and bring about a variety of physiological phenomena. A plant hormone which is called "brassinosteroid" has a variety of physiological effects on plants, including promotion at the cellular level such as promotion of cell elongation or cell division, regulation at the organ level such as opening of cotyledons, hypocotyl elongation, differentiation of vascular bundle, epinasty of green leaves, petiole elongation, or stem elongation, imparting of environmental stress tolerance such as cold tolerance, salt tolerance, and desiccation tolerance, and promotion of plant disease resistance through plant innate immune activation. Thus, it is effective to give brassinosteroid to plants for promotion of plant growth, crop yield increase, enhancement of tolerance to environmental stress, and the like. However, although brassinosteroid is recognized to have useful effects as described above in development of breeding of crop, etc., it has not been actually used in agriculture and plant biomass production in large quantities because it is expensive and problematic in terms of penetration into plants, migration, stability, etc.

In addition, although the most part of research on biosynthesis of brassinosteroid has been revealed, how brassinosteroid functions in plants has not been elucidated. Therefore, elucidation of the function has been awaited from the viewpoints of basic research and applied research. The BIL1 gene was identified as the causative gene for the bil1 (brz-insensitive-long hypocotyl1) mutant having a longer hypocotyl than that of the wild-type plant (Non-Patent Documents 1 and 2) as a result of chemical biology research using "brassinazole (Brz)" which is an inhibitor capable of freely regulating biosynthesis of brassinosteroid. Thereafter, the BIL1-derived protein, i.e., the "BIL1 protein," was found to be a transcription factor that regulates expression of many types of genes (approximately 3,000 types) among approximately 30,000 types of genes on the genome of *Arabidopsis* used as an experimental plant. At present, it is considered that the BIL1 protein is the master transcription factor (i.e., a factor that causes a chain reaction of gene expression) of brassinosteroid signaling.

The BIL1 protein is important in view of the wide range of subjects of transcription regulation. In addition, it is known to show interesting in-depth dynamics, by which the BIL1 protein is transferred into the nucleus from the cytosol with the addition of brassinosteroid. However, the detailed mechanism of regulation of transfer into the nucleus has not been elucidated.

PRIOR ART DOCUMENTS

Non-Patent Documents

Non-Patent Document 1: Asami, T., Nakano, T., and Nakashita, H. (2003). The influence of chemical genetics on plant science: shedding light on functions and mechanism of action of brassinosteroids using biosynthesis inhibitors, J. plant growth Regul. 22: 336-349.

Non-Patent Document 2: Wang, Z.-Y., Bai, M.-Y., Oh, E., and Zhu, J.-Y. (2012), Brassinosteroid signaling network and regulation of photomorphogenesis, Annu. Rev. Genet. 46: 701-724.

SUMMARY OF THE INVENTION

Problems to be Solved by the Invention

Therefore, an object of the present invention is to elucidate the mechanism of plant growth regulation by brassinosteroid and the mechanism of transfer of the BIL1 protein that is the master transcription factor of brassinosteroid signaling into the nucleus, discover new factors involved in the mechanisms, and using the factors for plant growth regulation, thereby increasing production of plant biomass or crop.

Means for Solving the Problem

As a result of intensive studies to achieve the above object, the present inventors found bss1 (brz-sensitive short hypocotyl 1) which is a mutant having a shorter hypocotyl length than that of the wild type plant from among *Arabidopsis* plants treated with Brz that is a brassinosteroid biosynthesis inhibitor, thereby identifying, as the causative gene for the bss1 mutant, a gene encoding the BSS1 protein having an ankyrin repeat domain that interacts BIL1 The present inventors further analyzed the BSS1 protein. As a result, it was found that: the BSS1 protein shows rare dynamics involving "oligomerization" and "monomerization," which cannot be seen in physiologically active substances such as other plant hormones, in response to an increase or decrease of brassinosteroid; the BSS1 protein binds to the BIL1 protein so as to be trapped within the cytosol under the brassinosteroid-deficient conditions, thereby inhibiting the transfer of the BIL1 protein into the nucleus, which results in reduction of plant stem elongation and plant length; and the BIL1 protein is released so as to be transferred to the nucleus under the brassinosteroid-supplemented conditions, resulting in promotion of plant stem elongation and leading to plant length elongation. These results revealed the new regulation mechanism in which regulation of plant growth (plant length elongation) is controlled by dynamics of the BSS1 protein involving "oligomerization" and "monomerization." The present invention has been completed based on such findings.

Specifically, the present invention encompasses the following inventions.

(1) A transgenic plant, in which expression of the BSS1 gene is suppressed or promoted.

(2) A transgenic plant, in which expression of any one of the following genes (a) to (f) is suppressed or promoted:

(a) a gene comprising DNA that consists of the nucleotide sequence shown in SEQ ID NO: 2 or 5;

(b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(d) a gene encoding a protein that consists of the amino acid sequence shown in SEQ ID NO: 3 or 6;

(e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling.

(3) The transgenic plant according to (1) or (2), wherein the plant is in the form of a plant body, a plant organ, a plant tissue, or a cultured plant cells.

(4) The transgenic plant according to any one of (1) to (3), wherein the plant is a monocotyledonous plant or a dicotyledonous plant.

(5) A method for regulating plant growth, which comprises suppressing or promoting expression of the BSS1 gene in a plant body.

(6) A method for regulating plant growth, which comprises suppressing or promoting expression of any one of the following genes (a) to (f) in a plant body:

(a) a gene comprising DNA that consists of the nucleotide sequence shown in SEQ ID NO: 2 or 5;

(b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(d) a gene encoding a protein that consists of the amino acid sequence shown in SEQ ID NO: 3 or 6;

(e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling.

(7) A method for producing a growth-regulated plant, which comprises suppressing or promoting expression of the BSS1 gene in a plant body.

(8) A method for producing a growth-regulated plant, which comprises suppressing or promoting expression of any one of the following genes (a) to (f) in a plant body:

(a) a gene comprising DNA that consists of the nucleotide sequence shown in SEQ ID NO: 2 or 5;

(b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(d) a gene encoding a protein that consists of the amino acid sequence shown in SEQ ID NO: 3 or 6;

(e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling.

(9) The method according to any one of (5) to (8), wherein the plant is in the form of a plant body, a plant organ, a plant tissue, or cultured plant cells.

(10) The method according to any one of (5) to (8), wherein the plant is a monocotyledonous plant or a dicotyledonous plant.

(11) A method for increasing biomass of a plant, which comprises suppressing expression of any one of the following genes (a) to (f):

(a) a gene comprising DNA that consists of the nucleotide sequence shown in SEQ ID NO: 2 or 5;

(b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(d) a gene encoding a protein that consists of the amino acid sequence shown in SEQ ID NO: 3 or 6;

(e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling.

(12) The method according to (11), wherein increasing biomass means promotion of plant length or stem length elongation, promotion of vascular bundle differentiation, petiole elongation, or leaf epinasty.

The present application claims the priority to U.S. Provisional Patent Application No. 62/108,327 filed on Jan. 27, 2015, and the contents of the patent application are herein incorporated by reference.

Effects of the Invention

According to the present invention, a method for regulating plant growth is provided, the method using the BSS gene that has been identified as the causative gene for the bss1 (brz-sensitive short hypocotyl 1) mutant, in which the effect of suppressing hypocotyl elongation via treatment with Brz (brassinosteroid biosynthesis inhibitor) is greater than that of the wild-type plant. The BSS gene has activity to down-regulate brassinosteroid signaling. It is therefore becomes possible to regulate plant growth (e.g., plant length or stem length elongation, vascular bundle differentiation, leaf epinasty, or petiole elongation) by suppressing or promoting expression of the BSS gene in a plant body, which is expected to lead to production of plant biomass in large quantities or development of fundamental technology for promotion of carbon dioxide fixation to plants.

BRIEF DESCRIPTION OF DRAWINGS

FIG. 1A shows phenotypes of wild-type (WT), bss1-1D, and BSS1-OX grown in the dark for 7 days on medium containing DMSO or 3 μM Brz (scale bar: 1 mm). FIG. 1B shows hypocotyl length of wild-type (WT), bss1-1D, and BSS1-OX grown in the dark for 7 days on medium containing different concentrations of Brz. The results are presented as the mean±s.d. (n>30). FIG. 1C shows phenotypes of wild-type (WT), bss1-1D, and BSS1-OX grown in soil under long-day conditions for 30 days. The right panel shows the phenotypes after 40 days. FIG. 1D shows leaf morphology of wild-type (WT) and bss1-1D. FIG. 1E shows a diagram of the genomic region flanking the T-DNA insertion site in bss1-1D. FIG. 1F shows qRT-PCR analysis of the expression levels of BSS1/BOP1 (At3g57130) in light-grown wild-type (WT), bss1-1D, and BSS1-OX lines shown in FIG. 1C. The results are presented as the mean±s.d. from 4 independent experiments. For all qRT-PCR analyses, ACT2 was used as the internal control.

EMBODIMENTS FOR CARRYING OUT THE INVENTION

Figure 2:
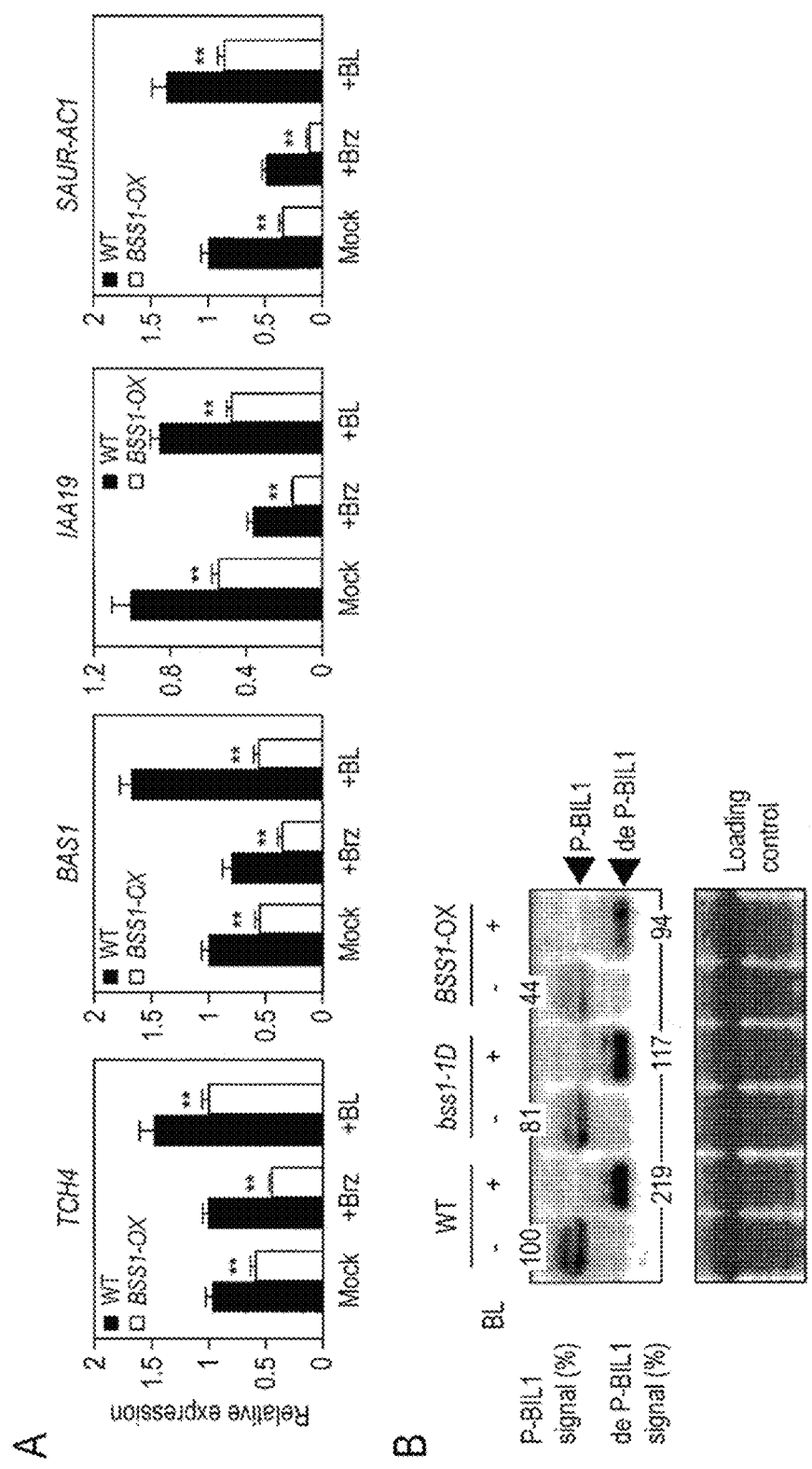
FIG. 2A shows Brz and BL responsiveness of BR-regulated genes in wild-type (WT) and BSS1-OX. The expression level of TCH, BAS1, IAA19, and SAUR-AC1 were analyzed by qRT-PCR in 7-day-old dark-germinated seedlings and treated with medium containing DMSO (Mock), 3 μM Brz (+Brz), or 100 nM BL (+BL) for 3 hours. The data represent the mean±s.d. of 4 independent experiments (**P<0.01, Student's t-test).
FIG. 2B shows immunoblot analysis of BIL1 phosphorylation status of wild-type (WT), bss1-1D, and BSS1-OX. Ten-day-old seedlings grown on medium with Brz were treated with 100 nM BL or mock solution for 3 hours. Total proteins were extracted and analyzed by immunoblotting with an anti-BIL1 antibody. P-BIL1 is phosphorylated BIL1 and de P-BIL1 is dephosphorylated BIL1 The upper panel shows an immunoblot of BIL1 protein extracted from wild-type (WT), bss1-1D, and BSS1-OX plants. The signal intensities of phosphorylated BIL1 (above) and dephosphorylated BIL1 (below) are shown by arrowhead, and each band signal is counted as a percentage relative to the level of phosphorylated BIL1 in WT seedlings. The lower panel shows a Ponceau S-stained gel.

The present invention is described in detail below.

1. BSS Gene

The present invention concerns the use of the BSS gene, which is a causative gene of the *Arabidopsis* bss1 (brz-sensitive short hypocotyl 1) mutant. According to the present invention, a method for regulating plant growth by regulating expression of the BSS gene is provided.

BSS genes have been widely preserved not only experimental *Arabidopsis* plants but also rice, maize, sugar cane, and the like beyond the plant species and a BSS gene derived from any plant can also be used. Examples of plants from which plant BSS genes are derived include, but are not limited to, monocotyledon plants such as rice, barley, wheat, corn, sugar cane, lawn grass, sorghum, millet, and Japanese millet and dicotyledon plants such as soybean, rapeseed, tomato, and potato.

For example, the BSS gene of *Arabidopsis* (AtBSS gene) has the genomic DNA sequence shown in SEQ ID NO: 1 and the cDNA sequence shown in SEQ ID NO: 2. The open reading frame (ORF) of the BSS gene consists of a region between the base at position 278 and the base at position 826 (549 bases) of the nucleotide sequence shown in SEQ ID NO: 1 and encodes a protein comprising the amino acid sequence (182 amino acids) shown in SEQ ID NO: 3. The BSS gene of rice (OsBSS gene) has the genomic DNA sequence shown in SEQ ID NO: 4 and the cDNA sequence shown in SEQ ID NO: 5. The open reading frame (ORF) of the BSS gene consists of a region between the base at position 1 and the base at position 528 and a region between the base at position 1497 and the base at position 2453 (1485 bases) of the nucleotide sequence shown in SEQ ID NO: 4 and encodes a protein comprising the amino acid sequence (494 amino acids) shown in SEQ ID NO: 6.

As the BSS gene used in the present invention, it is possible to use a homolog BSS gene consisting of a nucleotide sequence similar to the nucleotide sequence shown in SEQ ID NO: 2 or 5 as well as the AtBSS gene consisting of the sequence shown in SEQ ID NO: 2 and the OsBSS gene shown in SEQ ID NO: 5, as long as they have the function comparable to that of the BSS gene. Such homolog BSS gene may be a naturally occurring gene or an artificially prepared gene. For example, it may be homologs (including orthologs and paralogs) of the nucleotide sequences shown in the above sequence identification numbers or artificially mutated genes.

Therefore, the BSS gene used in the present invention includes the following genes:

(a) a gene comprising DNA that consists of the nucleotide sequence shown in SEQ ID NO: 2 or 5;

(b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;

(d) a gene encoding a protein that consists of the amino acid sequence shown in SEQ ID NO: 3 or 6;

(e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling.

The term "stringent conditions" as used herein refers to the conditions under which so-called specific hybrids are formed but non-specific hybrids are not formed. A person skilled in the art can adequately select the stringent hybridization conditions by referring to Sambrook et al., Molecular Cloning, A Laboratory Manual, 3rd Ed., Cold Spring Harbor Laboratory (2001). For example, hybridization is carried out by performing pre-hybridization in a hybridization solution containing 25% formamide, or 50% formamide for more stringent conditions, 4×SSC, 50 mM HEPES (pH 7.0), 10× Denhart's solution, and 20 µg/ml denatured salmon sperm DNA at 42° C. overnight, adding a labeled probe thereto, and incubating the resultant at 42° C. overnight. In the subsequent step of washing, the washing solution and temperature conditions are approximately "1×SSC, 0.1% SDS, 37° C.," approximately "0.5×SSC, 0.1% SDS, 42° C." for more stringent conditions, and approximately "0.2×SSC, 0.1% SDS, 65° C." for even more stringent conditions. The degree of stringency is increased as the temperature becomes higher and the salt concentration becomes lower. This enables isolation of a gene with higher identity.

It should be noted that the combinations of SSC, SDS, and temperature conditions described above are examples. A person skilled in the art can adequately combine the above or other factors that determine the hybridization stringency (e.g., probe concentration, probe length, and hybridization reaction duration) to realize stringency similar to that described above.

DNA obtained by hybridization carried out under the above stringent conditions usually has high identity to DNA represented by the nucleotide sequence shown in SEQ ID NO: 2 or 5. The term "high identity" as used herein refers to the sequence identity of at least 60% or higher, preferably 70% or higher, 80% or higher, or 85% or higher, more preferably 90% or higher, further preferably 95% or higher, and most preferably 97% or higher (e.g., 98% to 99%) to any of the nucleotide sequences shown in the above sequence identification numbers.

In relation to the expression "amino acid sequence derived by deletion, substitution, or addition of 1 or several amino acids," the number of amino acids that may be deleted, substituted, or added is the number of amino acids that can be deleted, substituted, or added in accordance with a known method for preparing mutant proteins, such as site-directed mutagenesis. The number is not limited as long as "activity to bind to a brassinosteroid master transcription factor BIL1 protein to inhibit the transfer of the BIL1 protein into the nucleus, thereby down-regulating brassinosteroid signaling" is maintained. Usually, the number is for example, 1 to 20, preferably 1 to 10, more preferably 1 to 7, and further preferably 1 to 5. Here, examples of substitution with other amino acids include substitution between hydrophobic amino acids (Ala, Ile, Leu, Met, Phe, Pro, Trp, Thr, and Val), hydrophilic amino acids (Arg, Asp, Asn, Cys, Glu, Gln, Gly, His, Lys, Ser, and Thr), amino acids having an aliphatic side chain (Gly, Ala, Val, Leu, Ile, and Pro), and amino acids having a hydroxyl-group-containing side chain (Ser, Thr, and Tyr). The term "mutation" used herein primarily means a mutation that is artificially introduced in accordance with a known method for preparing mutant proteins, although a naturally occurring similar mutation may be employed. It has been known that a polypeptide having an amino acid sequence derived from a given amino acid sequence by deletion or addition of 1 or several amino acid residues and/or substitution with a different amino acid maintains its biological activity.

The term "60% or higher identity" used in relation to the amino acid sequence refers to sequence identity of preferably 70% or higher, preferably 80% or higher, or 85% or higher, more preferably 90% or higher, further preferably 95% or higher, and most preferably 97% or higher (e.g., 98% to 99%).

The term "sequence identity" used herein refers to a value calculated by aligning at least two sequences to be compared, determining identical residues present in each sequence, determining the number of matching sites, dividing the number of the matching sites by the total number of residues in the sequence regions to be compared, and multiplying the obtained value by 100. Identity of sequence can be determined using the BLASTN (at the nucleic acid level) or BLASTX (at the amino acid level) program.

The BSS gene used in the present invention can be prepared using a known technique. For example, total mRNA may be prepared from an *Arabidopsis thaliana* or rice tissue extract, primers may be designed based on the nucleotide sequence shown in SEQ ID NO: 2 or 5, and full-length cDNA of the nucleotide sequence shown in the above sequence identification number can be obtained by performing the RACE method or the like. Alternatively, a cDNA library may be prepared from an *Arabidopsis thaliana* or rice tissue extract, a probe may be designed based on the nucleotide sequence shown in the above sequence identification number, and the gene can be obtained using the hybridization method. Further, the gene may be artificially synthesized based on the nucleotide sequence shown in the above sequence identification number.

A person skilled in the art can readily obtain a homolog of the BSS gene by referring to, for example, Molecular Cloning (Sambrook, J. et al., Molecular Cloning: A Laboratory Manual 3rd ed., Cold Spring Harbor Laboratory Press, 10 Skyline Drive Plainview, N.Y., (2001)).

For example, deletion, addition, and substitution of amino acids can be carried out by introducing a mutation into a gene encoding the above protein using a technique known in the art. Mutation can be introduced into a gene by a known technique such as the Kunkel method or the Gapped duplex method, or a method in accordance therewith. For example, a kit for introducing mutation that utilizes the site-directed mutagenesis method (e.g., Mutant-K (TAKARA) or Mutant-G (TAKARA)), or the kit of LA PCR in vitro Mutagenesis series (TAKARA)) can be used. Alternatively, a sequence having a mutation being introduced into the nucleotide sequence shown in the above sequence identification number may be synthesized using a commercially available nucleic acid synthesis apparatus.

2. Transgenic Plant and Method for Producing the Same

The transgenic plant of the present invention can be produced via transformation of a plant of interest by suppressing or promoting expression of the BSS gene in the plant body. Suppression of expression of the BSS gene includes suppression of transcription of the BSS gene and suppression of translation of the BSS gene into a protein. Suppression of the expression also includes reduction of the expression as well as complete silencing of the expression. On the other hand, promotion of expression of the BSS gene includes promotion of transcription of the BSS gene and promotion of translation of the BSS gene into a protein. Promotion of the expression also includes an increase of the expression as well as overexpression.

Transgenic plants in which expression of the BSS gene is suppressed can be produced by suppressing expression of the BSS gene present in a plant body. Examples of a method for suppressing expression of the BSS gene include the antisense method, the RNAi method, the ribozyme method, and the co-suppression method. These methods are conducted by introducing DNA that suppresses expression of the endogenous BSS gene. The term "endogenous BSS gene" used herein refers to the BSS gene originally present in a plant to be transformed.

In the antisense method, DNA that suppresses expression of the BSS gene, which is used herein, is antisense DNA that encodes RNA (antisense RNA) having a sequence complementary to a whole or a part of mRNA transcribed from the gene. Antisense DNA binds to its complementary strand, i.e., mRNA that is a transcription product of the BSS gene, thereby making it possible to inhibit translation of the BSS gene and suppress expression of the gene. The nucleotide sequence length of antisense DNA encoding antisense RNA is not necessarily the full length of the nucleotide sequence of mRNA of the BSS gene and it may be a partial length thereof as long as expression of the BSS gene can be suppressed. Such partial length is a length corresponding to 30%, preferably 50%, more preferably 80%, and further preferably 90% of the full-length nucleotide sequence of mRNA of the BSS gene.

Antisense DNA is ligated in the antisense direction to the recombinant vector. Ligation may be established directly or via a linker. Antisense DNA is ligated to the vector in a manner such that when antisense DNA is transcribed in a host, antisense RNA that hybridizes to mRNA of the BSS gene is generated, and then, the vector is introduced into plant cells. In order to ligate antisense DNA to the vector such that antisense RNA is generated, antisense DNA is ligated downstream of the DNA fragment having a promoter sequence in the antisense direction (opposite direction) such that it is transcribed into RNA by the operation of the promoter.

In the RNAi method, it is also possible to use, as DNA that suppresses expression of the BSS gene, DNA encoding RNA that suppresses expression of the BSS gene via RNA interference (RNAi), i.e., DNA in which an inverted repeat sequence identical or similar to the sequence of the BSS gene is arranged. The term "RNA interference" refers to a phenomenon in which when DNA, in which an inverted repeat sequence identical or similar to the sequence of the target gene is arranged, is introduced into a host via transformation, double-stranded RNA from the introduced DNA is expressed and expression of the target gene is suppressed. RNA interference is believed to proceed by the following steps: (i) a step in which mRNA of the target gene and double-stranded RNA from the introduced sequence (double-strand RNA, dsRNA) form a complex referred to as "RNA-induced silencing complex (RISC)" and complementary RNA is synthesized using the associated sequence as a primer; (ii) a step in which the complex is fragmented by the endogenous RNase; and (iii) a step in which double-stranded RNA (small interfering RNA, siRNA) that has been fragmented into 20 to 30 base pairs serves as the signal of secondary RNA interference, thereby re-degrading mRNA of the target gene. The length of DNA used for the RNAi method may be the full length of the target gene; however, it may be a length of at least 20 bases, preferably 30 bases or more, and more preferably 50 bases or more.

The vector that expresses dsRNA capable of causing RNAi as hairpin dsRNA is preferably utilized for plant RNAi. This is a system for arranging the DNA sequence corresponding to a dsRNA formation part to form an inverted repeat (IR) at both ends of a linker (spacer) sequence having several or more bases, and transcribing hairpin dsRNA by a promoter that is highly expressed in a plant body, thereby producing siRNA within cells. In addition to the above hairpin-type system, there is also a tandem-type siRNA expression system. In the tandem-type system, sense RNA and antisense RNA are transcribed from two promoters and hybridize with each other within cells, thereby producing siRNA. Such RNAi vector can be readily constructed in accordance with a known method in the art or using a commercially available RNAi vector or system (e.g., psiRNA (Invitrogen) or pSUPER RNAi System™ (Oligo-Engine)).

In the ribozyme method, as a DNA that suppresses expression of the BSS gene, a DNA encoding a ribozyme that is designed to specifically cleave mRNA which is a transcription product of the BSS gene is used. Some ribozymes having an active domain of approximately 40 nucleotides are called hammerhead or hairpin ribozymes, any of which can be used in the present invention. When DNA encoding such ribozyme is used, it may be linked to a promoter and a transcription termination sequence within the recombinant vector so that it is transcribed in plant cells. It is also possible to dispose another trimming ribozyme acting on cis elements for trimming in plant cells on the 5 'side and 3' side of the ribozyme portion. Thus, it is possible to precisely cut out only a ribozyme portion from RNA containing the transcribed ribozyme.

In the co-suppression method, as DNA that suppresses expression of the BSS gene, DNA encoding RNA that suppresses expression of the BSS gene by co-suppression effects, i.e., DNA having a sequence identical or similar to the sequence of the BSS gene is used. The term "co-suppression" refers to a phenomenon in which when DNA having a sequence identical or similar to the sequence of the target gene is introduced into a host via transformation, expression of both the introduced exogenous gene and the target gene is suppressed. The gene to be used for co-suppression does not need to be completely identical to the BSS gene as a target; however, it has at least 70%, preferably 80% or more, and more preferably 90% or more sequence identity.

Further, transgenic plants in which expression of the BSS gene is suppressed can be produced by disrupting the BSS gene present in a plant or inhibiting activity of the BSS gene. Examples of the method for disrupting the BSS gene or inhibiting activity of the BSS gene include insertion of T-DNA, insertion of transposon, fast neutron irradiation, ion beam irradiation, treatment with mutagens [alkylating agent (N-ethyl-N-nitrosourea (ENU), N-methyl-N'-nitro-N-nitrosoguanidine (NTG), ethyl methanesulfonate (EMS), etc.); base analogs (BrdU, etc.); polycyclic aromatic hydrocarbons (benzopyrene, chrysene, etc.); DNA intercalators (ethidium bromide, etc.); and DNA crosslinking agents (cisplatin, mitomycin C, etc.)], insertion of a gene having a dominant negative trait, and introducing a mutation or deletion into the BSS gene via treatment using a site-specific DNA degrading enzyme (e.g., Zinc Finger Nuclease (ZFN), Transcriprion Acriator Like Effector Nucease (TALEN)). In the site-directed mutagenesis method, the mutation (e.g., substitution) introducing site may be any site where the activity of the BSS protein encoded by the gene is inhibited after mutagenesis, and it is preferably a site where the activity of BSS protein encoded by the gene disappears after mutagenesis. Examples of mutation to be introduced include frameshift mutation, nonsense mutation, and missense mutation. Of these, frameshift mutation or nonsense mutation is preferred.

Meanwhile, transgenic plants in which expression of the BSS gene is promoted can be produced by introducing the BSS gene in the sense direction. Therefore, a method for suppressing expression of the BSS gene or a method for promoting expression of the BSS gene may be selected and carried out in accordance with the trait of interest.

Basically, vectors used in the above method for suppressing or promoting expression of the BSS gene may be general recombinant vectors for plant transformation. Examples of vectors that can be preferably used include pBI, pPZP, pSMA, and pCAMBIA vectors which can introduce the BSS gene or DNA that suppress expression of the BSS gene (referred to as "target genes") into a plant via *Agrobacterium*. Use of pBI binary vectors or intermediate vectors is particularly preferable, and examples thereof include pBI121, pBI101, pBI101.2, and pBI101.3. The term "binary vector" refers to a shuttle vector replicable in *Escherichia coli* and *Agrobacterium*. When a plant is infected with *Agrobacterium* that harbors a binary vector, DNA located in a region defined by the border sequences (LB sequence and RB sequence) on the vector can be integrated into plant nuclear DNA. On the other hand, pUC vectors are capable of directly introducing a gene into a plant, and examples thereof include pUC18, pUC19 and pUC9. Further, plant virus vectors, such as cauliflower mosaic virus (CaMV), bean golden mosaic virus (BGMV), and tobacco mosaic virus (TMV) vectors, can also be used.

When a binary vector plasmid is used, a target gene is inserted into a site between border sequences (LB and RB sequences) of the binary vector, and the recombinant vector is amplified in *Escherichia coli*. Subsequently, the amplified recombinant vector is introduced into, for example, *Agrobacterium tumefaciens* GV3101, C58, LBA4404, EHA101 or EHA105, or *Agrobacterium rhizogenes* LBA1334, by the electroporation method or the like, and the *Agrobacterium* is used for plant transduction.

For inserting a target gene into a vector, one may employ a method in which purified DNA is first cleaved with an adequate restriction enzyme and the cleaved fragment is then inserted into a restriction enzyme site or multicloning site of adequate vector DNA to connect the fragment to the vector.

In addition, a promoter, an enhancer, a terminator, a replication origin that allows the use of a binary vector (e.g., a replication origin derived from Ti or Ri plasmid), a selection marker gene, and the like can be connected to a site upstream, inside, or downstream of the target gene in the recombinant vector.

A "promoter" may not be derived from a plant, provided that it is DNA that can function in a plant cell and bring about expression in a given tissue or at a given growth stage of a plant. Specific examples include cauliflower mosaic virus (CaMV) 35S promoter, nopaline synthase gene promoter (Pnos), maize-derived ubiquitin promoter, rice-derived actin promoter, and tobacco-derived PR protein promoter. When a target gene is to be expressed specifically in a given organ, a promoter that is expressed in a tissue-specific manner can be used. For example, the plant growth-regulating effect of the target gene of the present invention can be efficiently attained by using a vascular bundle-specific gene promoter.

An enhancer is used, for example, for increasing the expression efficiency of a target gene. Examples thereof include an enhancer region that comprises an upstream sequence in the CaMV 35S promoter.

Any sequence may be used as a terminator, provided that it can terminate transcription of a gene transcribed by a promoter. Examples thereof include terminators of the nopaline synthase (NOS) gene, the octopine synthase (OCS) gene, and the CaMV 35S RNA gene.

Examples of selection marker genes include ampicillin-resistant gene, neomycin-resistant gene, hygromycin-resistant gene, bialaphos-resistant gene, and dihydrofolate reductase gene.

The selection marker gene may be connected to a single plasmid together with a target gene to prepare a recombinant vector. Alternatively, a recombinant vector obtained by connecting the selection marker gene to a plasmid and a recombinant vector obtained by connecting a target gene may be separately prepared. When the vectors are separately prepared, the vectors are co-transfected (co-introduced) into a host.

The transgenic plant of the present invention can be produced by introducing the target gene into a target plant. In the present invention, the term "introduction of a gene" means that a target gene is introduced into cells of the above host plant in a manner that allows the gene to express using, for example, a known genetic engineering technique. The introduced gene may be integrated into the genomic DNA of a host plant or may be present being comprised in a foreign vector.

As a method for introducing the target gene into a plant as described above, one of a variety of methods that have been reported and established can be adequately utilized. Examples thereof include the *Agrobacterium* method, the PEG-calcium phosphate method, the electroporation method, the liposome method, the particle gun method, and the microinjection method. When the *Agrobacterium* method is employed, a protoplast, a tissue section, or a plant body as it is (i.e., the in planta method) may be used. When a protoplast is used, the introduction can be carried out using a method in which the protoplast is co-cultured with *Agrobacterium* harboring a Ti plasmid or an Ri plasmid (for *Agrobacterium tumefaciens* or *Agrobacterium rhizogenes*, respectively), or the protoplast is fused to *Agrobacterium* which has been converted to a spheroplast (the spheroplast method). When a tissue section is used, the introduction can be carried out using a method in which an aseptically cultured leaf disc of a target plant or a callus (cultured undifferentiated cell) is infected. When the in planta method using a seed or a plant body is employed (i.e., in a system that does not involve tissue culture with the addition of plant hormones), the introduction can be carried out by direct treatment of an imbibed seed, a young seedling (germ), a potted plant, or the like with *Agrobacterium*. These plant transformation methods can be carried out in accordance with the descriptions of general textbooks such as "Shinban, Model shokubutsu no jikken protocol, Idengakuteki shuhou kara genome kaiseki made (New edition, Experimental protocols for model plants, From genetic engineering technique to genome analysis), 2001, supervised by Isao Shimamoto & Kiyotaka Okada, Shujunsha."

One can confirm whether or not a target gene has been incorporated into a plant using the PCR method, the Southern hybridization method, the Northern hybridization method, the Western blotting method or the like. For example, DNA is prepared from a transgenic plant, primers specific for the target gene are designed, and PCR is then carried out. After PCR has been carried out, the amplification product is subjected to agarose gel electrophoresis, polyacrylamide gel electrophoresis, capillary electrophoresis or the like, and stained with ethidium bromide, a SYBR Green solution or the like. Transformation can be confirmed based on detection of the amplification product as a single band. Alternatively, the amplification product can be detected by carrying out PCR with the use of primers that have been labeled with a fluorescent dye or the like beforehand. Further, one may use a method in which the amplification product is bound to a solid phase such as a microplate, and confirmed using fluorescence, an enzymatic reaction or the like. Further, one may confirm that a target gene introduced into a plant cell is expressed (that is, the plant is transformed) by extracting proteins from the plant cell, fractionating the proteins by two-dimensional electrophoresis, and detecting a band of the protein encoded by the target gene.

Alternatively, a vector in which one of a variety of reporter genes (e.g., a gene for β-glucuronidase (GUS), luciferase (LUC), green fluorescent protein (GFP), chloramphenicol acetyltransferase (CAT) or β-galactosidase (LacZ)) is connected downstream of a target gene is prepared. *Agrobacterium* into which the aforementioned vector has been introduced is used to transform a plant in a manner similar to that as described above. Then, expression of the reporter gene is measured. Thereby, transformation of the plant can be confirmed.

The plant used for transformation in the present invention may be a monocotyledonous plant or a dicotyledonous plant. Examples of plants used for transformation in the present invention include plants belonging to the family Brassicaceae, the family Gramineae, the family Solanaceae, the family Leguminosae, the family Compositae, the family Arecaceae, the family Anacardiaceae, the family Cucurbitaceae, the family Rosaceae, the family Caryophyllaceae, the family Salicaceae, the family Myrtaceae, and the family Liliaceae, for example (see below).

The family Brassicaceae: *Arabidopsis thaliana*, rapeseed (*Aburana*) (*Brassica rapa, Brassica napus*), cabbage (*Brassica oleracea* var. *capitata*), rapeseed (*Natane*) (*Brassica rapa, Brassica napus*), rape blossoms (*Brassica rapa, Brassica napus*), Chinese cabbage (*Brassica rapa* var. *pekinensis*), qing-geng-cai (*Brassica rapa* var. *chinensis*), turnip (*Brassica rapa* var. *rapa*), nozawana (*Brassica rapa* var. *hakabura*), potherb mustard (*Brassica rapa* var. *lancinifolia*), komatsuna (*Brassica rapa* var. *peruviridis*), Chinese cabbage (*Paku Choi*) (*Brassica rapa* var. *chinensis*), radish (*Brassica Raphanus sativus*), wasabi (*Wasabia japonica*), etc.

The family Gramineae: corn (*Zea mays*), rice (*Oryza sativa*), barley (*Hordeum vulgare*), wheat (*Triticum aestivum*), bamboo (*Phyllostachys*), sugarcane (*Saccharum officinarum*), napier grass (*Pennisetum pupureum*), Erianthus (*Erianthus ravenae*), Japanese silver grass (*Miscanthus virgatum*), Sorghum (*Sorghum*), switchgrass (*Panicum*), etc.

The family Solanaceae: tobacco (*Nicotiana tabacum*), eggplant (*Solanum melongena*), potato (*Solaneum tuberosum), tomato (*Lycopersicon lycopersicum*), pepper (*Capsicum annuum*), petunia (*Petunia*), etc.

The family Leguminosae: soybean (*Glycine max*), pea (*Pisum sativum*), fava bean (*Vicia faba*), Japanese wisteria (*Wisteria floribunda*), peanut (*Arachis hypogaea*), *Lotus japonicus* (*Lotus corniculatus* var. *japonicus*), common bean (*Phaseolus vulgaris*), azuki (*Vigna angularis*), acacia (*Acacia*), etc.

The family Compositae: Chrysanthemum (*Chrysanthemum morifolium*), sunflower (*Helianthus annuus*), etc.

The family Arecaceae: oil palm (*Elaeis guineensis, Elaeis oleifera*), coconut (*Cocos nucifera*), Date Palm (*Phoenix dactylifera*), wax palm (*Copernicia*)

The family Anacardiaceae: hazenoki (*Rhus succedanea*), cashew (*Anacardium occidentale*), poison oak (*Toxicodendron vernicifluum*), mango (*Mangifera indica*), pistachio (*Pistacia vera*), etc.

The family Cucurbitaceae: pumpkin (*Cucurbita maxima, Cucurbita moschata, Cucurbita pepo*), cucumber (*Cucumis sativus*), Trichosanthes (*karasu uri*) (*Trichosanthes cucumeroides*), gourd (*Lagenaria siceraria* var. *gourda*), etc.

The family Rosaceae: almond (*Amygdalus communis*), rose (*Rosa*), strawberry (*Fragaria*), cherry (*Prunus*), apple (*Malus pumila* var. *domestica*), etc.

The family Caryophyllaceae: carnation (*Dianthus caryophyllus*), etc.

The family Salicaceae: poplar (*Populus trichocarpa, Populus nigra, Populus tremula*), etc.

The family Myrtaceae: eucalyptus (*Eucalyptus camaldulensis, Eucalyptus grandis*), etc.

The family Liliaceae: tulip (*Tulipa*), lily (*Lilium*), etc.

Examples of plant materials to be subjected to transformation in the present invention include: plant organs such as stems, leaves, seeds, embryos, ovules, ovaries, and shoot apices; plant tissues such as anthers and pollens, and the sections thereof; undifferentiated calluses; and cultured plant cells such as protoplasts which are prepared by removing cell walls from the above by enzyme treatment. When the in planta method is employed, an imbibed seed or a whole plant body can be utilized.

According to the present invention, the term "transgenic plant" means any one of a whole plant body, a plant organ (e.g., leaf, petal, stem, root, grain, or seed), a plant tissue (e.g., epidermis, phloem, parenchyma, xylem, or vascular bundle), or a cultured plant cell (e.g., callus).

When a cultured plant cell is to be used, an organ or an individual may be regenerated according to a known tissue culture method in order to regenerate a transformant from a resulting transformed cell. A person skilled in the art can readily carry out such a procedure using a method that is commonly known as a method of regenerating a plant body from a plant cell. For example, a plant body can be regenerated from a plant cell in the following manner.

At the outset, when a plant tissue or a protoplast is used as a plant material to be subjected to transformation, it is cultured in a medium for callus formation that has been sterilized after adding, for example, inorganic elements, vitamins, carbon sources, saccharides as energy sources or plant growth regulators (plant hormones, such as auxin, cytokinin, gibberellin, abscisic acid, ethylene, or brassinosteroid) to form a dedifferentiated callus which proliferates in an unstructured manner (hereinafter, this process is referred to as "callus induction"). The thus formed callus is transferred to a fresh medium containing plant growth regulators such as auxin, and then further proliferated (or subcultured).

Callus induction is carried out on a solid medium such as agar, and subculture is carried out, for example, in a liquid medium. Thereby, the cultivation can be carried out efficiently and in large quantities in the respective cases. Subsequently, the callus proliferated by the aforementioned subculture is cultured under adequate conditions to induce redifferentiation of an organ (hereinafter referred to as "induction of redifferentiation"), and a complete plant body is regenerated in the end. The induction of redifferentiation can be carried out by adequately setting the types and quantities of respective ingredients such as plant growth regulators (e.g., auxin) and carbon sources in the medium, light, temperature and the like. Such induction of redifferentiation results in formation of adventitious embryo, adventitious root, adventitious bud, adventitious shoot and the like, which further leads to growth into a complete plant body. Alternatively, storage may be conducted in a state prior to the formation of a complete plant body (e.g., encapsulated artificial seed, dry embryo, or freeze-dried cell or tissue).

The transgenic plants of the present invention also include plant bodies of progenies (T2 and T3 generations) obtained by sexual or asexual reproduction of plant bodies having a gene of interest being introduced (including plant bodies regenerated from transformed cells or calluses), and portions of tissues or organs of the progeny plants (seeds, protoplasts, and the like). The transgenic plant of the present invention can be produced in large quantities by obtaining a reproductive material such as a seed or a protoplast, from a plant body transformed by introduction of the target gene, and then cultivating or culturing the same.

Among transgenic plants obtained in the manner described above, down regulation of brassinosteroid signaling caused by BSS1 is cancelled in transgenic plants in which expression of the BSS1 gene is suppressed. This results in promotion of plant growth, thereby increasing biomass per plant. In the present invention, the term "biomass" refers to the amount of a plant body or a part thereof existing within an arbitrary space at a given time. The term is used to encompass substances, foods, materials, fuels, resources, and the like derived from said plant or parts thereof. Specifically, increased biomass refers to hypertrophy of a subterranean stem (rhizom, corm, tuber, bulb), a terrestrial stem, a flowering stem or a vine, hypertrophy of a seed, acceleration of elongation of stem length, plant length, culm length, or ear length, or enlargement of a source organ such as a leaf. Biomass increased by the present invention is characterized in that the height of a plant body increases 1.2 fold or more, preferably 1.5 fold or more, more preferably 2 fold or more over a control wild-type plant.

In addition, among transgenic plants obtained in the manner described above, down regulation of brassinosteroid signaling caused by BSS1 is induced, resulting in dwarfing of transgenic plants in which expression of the BSS1 gene is promoted. The term "dwarfing" typically refers to suppression of plant length elongation. Dwarfing is characterized in that the plant length of a plant body decreases 1.2 fold or more, preferably 1.5 fold or more, more preferably 2 fold or more over a control wild-type plant. The phenotype trait of having a short plant length means that a plant is resistant to wind damage due to a typhoon or the like and is unlikely to fall down even with an increase in the number of grains. In the case of rice, for example, it is possible to increase the number of rows for planting seedlings and to increase the density of planted seedlings per unit area. When a fruit tree (e.g., banana or mango) or a palm tree (e.g., date palm or coconut palm) with a height that may be several meters is imparted with such trait, it is advantageous in that harvesting of fruits can be easily carried out, and yield per unit resource (water, a fertilizer, etc.) increases, for example.

EXAMPLES

The present invention is hereafter described in greater detail with reference to the following examples, although the present invention is not limited thereto.

The materials and methods used in the Examples are described below.

[Materials and Methods]

(1) Plant Materials and Growth Conditions

Arabidopsis thaliana ecotype Columbia (Col-0) was used as the wild-type plant. The seeds were germinated on ½ Murashige and Skoog (MS) medium (Duchefa) with 0.8% phytoagar (Duchefa) and 1.5% sucrose and were subsequently transferred to soil. The plants were grown at 22° C. under white light (a 16-h light/8-h dark cycle for long-day conditions).

(2) Screening for the Bss1-1D Mutant

Approximately 10,000 RIKEN GSC Arabidopsis activation-tagging lines (Nakazawa et al., 2003, Activation tagging, a novel tool to dissect the functions of a gene family. Plant J. 34: 741-750) were screened on ½ MS medium containing 3 µM Brz (Asami et al., 2000, Characterization of brassinazole, a triazole-type brassinosteroid biosynthesis inhibitor, Plant Physiol. 123: 93-100). After growth for 7 days in the dark, seedlings with shorter hypocotyls than those of the controls were identified and transferred to soil. Inverse PCR was used to amplify the flanking genomic sequences of the T-DNA of pPCVICE4HPT as previously described (Bradshaw Jr., 2005, Mutations in CAX1 produce phenotypes characteristic of plants tolerant to serpentine soils, New Phytol. 167: 81-88). The total RNA was extracted from dark-grown 3-day-old seedlings of wild-type and bss1-1D plants using an RNeasy Plant Mini Kit (QIAGEN). First-strand cDNA was synthesized with PrimeScript (Takara) and used in quantitative real-time PCR (qRT-PCR). The qRT-PCR analysis was performed according to the instructions provided for the Thermal Cycler Dice (Takara) using a SYBR Premix ExTaq system (Takara). The following gene-specific primers were used for qRT-PCR analysis: (for BSS1) 5'-CATGACCTAACCTCGACTTT-3' (SEQ ID NO: 7) and 5'-CCCATCACCATTAGCTTC-3' (SEQ ID NO: 8); (for the constitutively expressed control gene ACT2) 5'-CGCCATCCAAGCTGTTCTC-3' (SEQ ID NO: 9) and 5'-TCACGTCCAGCAAGGTCAAG-3' (SEQ ID NO: 10).

(3) Generation of Transgenic Plants

To recapitulate the bss1-1D phenotype and analyze the subcellular localization, BSS1 cDNA without a stop codon was amplified from Arabidopsis Col-0 cDNA using the BSS1-Forward 5'-CACCATGAGCAATACTTC-GAAGAATCACTCAAA-3' (SEQ ID NO: 11) and BSS1-Reverse 5'-GAAATGGTGGTGGTGGTGATGATACATC-3' (SEQ ID NO: 12) primers, cloned into pENTR/D-TOPO (Invitrogen), and subsequently cloned using the Gateway strategy (Invitrogen) into the binary vector pGWB5 (Nakagawa et al., 2007, Development of series of gateway binary vectors, pGWBs, for realizing efficient construction of fusion genes for plant transformation. J. Biosci. Bioeng. 104: 34-41) containing a CaMV 35S promoter and GFP. BSS1 cDNA was cloned between CaMV 35S promoter and GFP.

To construct the BSS1 promoter fused with GUS and BSS1 fused with GFP driven by its own promoter, a 1.0-kb fragment including the first exon and promoter region and a 3.0-kb fragment including the coding region and promoter region, respectively, were amplified from Arabidopsis Col-0 genomic DNA using the BSS1-GUS-Forward 5'-CAC-CATATGGTCGATCCCAAACCAACAGGAGAA-3' (SEQ ID NO: 13) and BSS1-GUS-Reverse 5'-AG-TAAGCAACGCGAGCTGCTCGACGCCAAAGTA-3' (SEQ ID NO: 14) primers for the GUS construct and the BSS1-GFP-Forward 5'-CACCATATGGTCGATC-CCAAACCAACAGGAGAA-3' (SEQ ID NO: 15) and BSS1-GFP-Reverse 5'-GAAATGGTGGTGGTGGTGAT-GATACATC-3' (SEQ ID NO: 16) primers for the GFP construct.

The amplified products were cloned into pENTR/D-TOPO (Invitrogen) and subsequently cloned into the binary vectors pGWB3 and pGWB4 using the Gateway strategy (Invitrogen). To analyze the subcellular localization of BIL1, cDNA without a stop codon was amplified using the BIL1-Forward 5'-CACCATGACTTCGGATGGAGCTAC-3' (SEQ ID NO: 17) and BIL1-Reverse 5'-ACCACGAGC-CTTCCCATTTCC-3' (SEQ ID NO: 18) primers, cloned into pENTR/D-TOPO (Invitrogen), and subsequently cloned into the binary vector pGWB5. The resulting CaMV 35S-BSS1-GFP, CaMV 35S-BIL1-GFP, BSS1 promoter:BSS1-GFP, and BSS1 promoter: GUS fusion constructs were transformed into Col-0 via the floral dipping method (Clough and Bent., 1998). The transgenic plants were screened on ½ MS medium containing 25 mg/L kanamycin.

(4) Quantitative Real-Time PCR (qRT-PCR)

Total RNA was extracted from plants using an RNeasy Plant Mini Kit (QIAGEN).

The first-strand cDNA was synthesized using PrimeScript (Takara) and was used in qRT-PCR. The qRT-PCR was performed according to the instructions provided for the Thermal Cycler Dice (Takara) using the SYBR Premix ExTaq system (Takara). The following primers were used: (for TCH4) TCH4-Forward 5'-CGAGTCTTGGAACGCT-GAT-3' (SEQ ID NO: 19) and TCH4-Reverse 5'-CTTCTT-GTTGAAAGCCACGG-3' (SEQ ID NO: 20) primers; (for BAS1) BAS1-Forward 5'-GCCAAATTGACACTCGCTG-TAA-3' (SEQ ID NO: 21) and BAS1-Reverse 5'-GACGG-TAGGTGCATGCTGATAA-3' (SEQ ID NO: 22) primers; (for IAA19) IAA19-Forward 5'-GAAGGACTCGGGCTT-GAGAT-3' (SEQ ID NO: 23) and IAA19-Reverse 5'-GACGCCGCTTTCACATTG-3' (SEQ ID NO: 24) primers; and (for SAUR) SAUR-AC1-Forward 5'-GAGATAT-GTGGTGCCGGTTT-3' (SEQ ID NO: 25) and SAUR-AC1-Reverse 5'-GTATTGTTAAGCCGCCCATT-3' (SEQ ID NO: 26) primers.

(5) GUS Staining

The seedlings of the BSS1 promoter: GUS transgenic plants were used for the histochemical detection of GUS expression. The samples were stained at 37° C. overnight in GUS staining solution as previously described (Ito and Fukuda, 2002, ZEN1 is a key enzyme in the degradation of nuclear DNA during programmed cell death of tracheary elements. Plant Cell 14: 3201-3211). To test the induction of GUS expression, 3-day-old transgenic seedlings were grown on medium with 3 µM Brz or dimethyl sulfoxide (DMSO) as a control.

(6) Fluorescence Microscopic Observation

The plants that were transformed with the CaMV35S-BSS1-GFP construct BSS1(-GFP)-OX and the CaMV35S-BIL1-GFP construct BIL1-GFP-OX were observed via confocal laser scanning microscopy with a BX60 fluorescence microscope (Olympus) equipped with a Model CSU10 confocal scanner (Yokogawa Electric) and LSM700 (Zeiss).

(7) BFA Treatment and FM4-64 Staining

FM4-64 (Molecular Probes) dissolved in water was applied to *Arabidopsis* plants at a final concentration of 4 μM for 3 minutes. The plants were washed with water to remove the excessive amount of the stain and observed. A DMSO-base stock solution of Brefeldin A (BFA) (Sigma) was applied to the cells at a final concentration of 50 μM for 1 hour.

(8) Analysis of Signal Intensities

Figure 9:
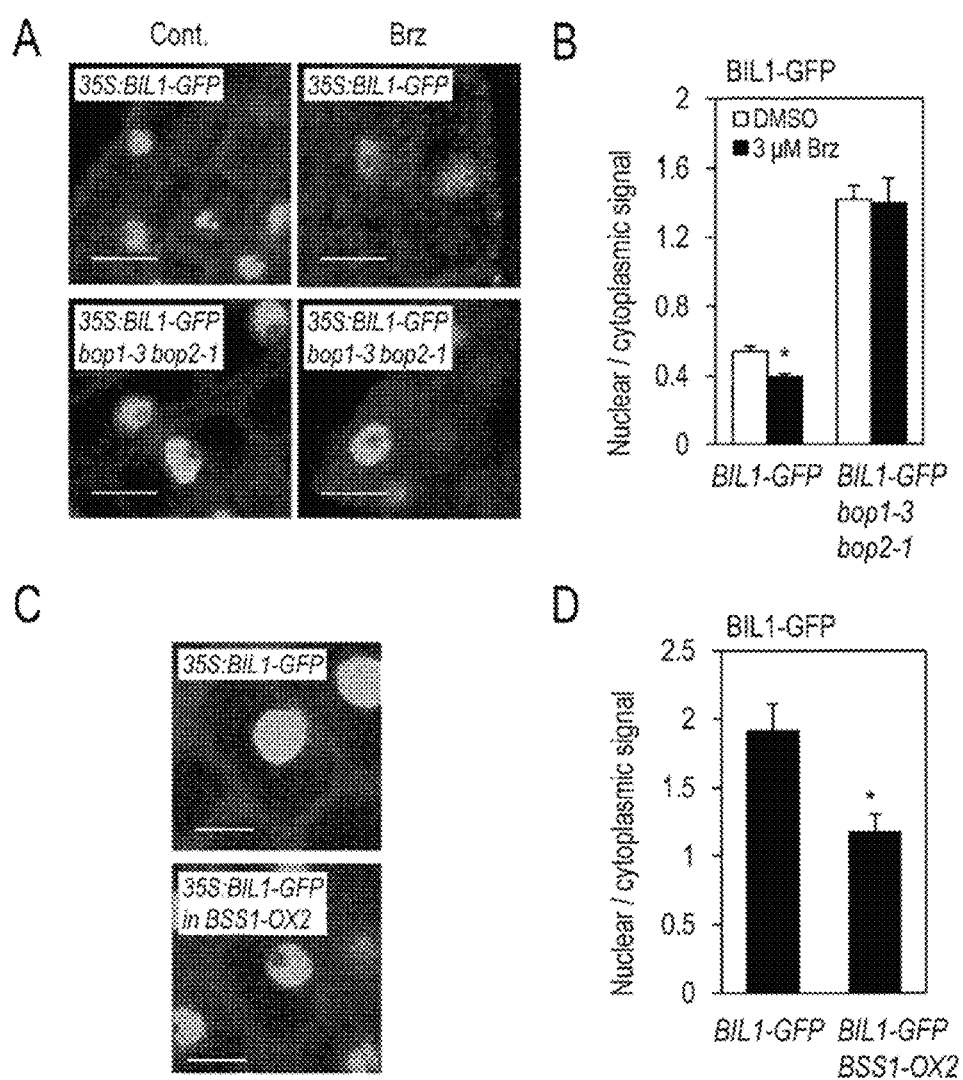
FIG. 9A shows images of BIL1-GFP in root cells of 4-day-old wild-type (WT) or bop1-3 bop2-1 seedlings grown on medium containing DMSO (Cont.) or 3 μM Brz (Brz) (scale bar: 10 μm).
FIG. 9B shows the ratio of the nuclear-to-cytosolic signal intensity in the root cells of 4-day-old wild-type (WT) and bop1-3 bop2-1 seedlings. The results are presented as the mean±s.d. (n=61, *P<0.01, Student's t-test).
FIG. 9C shows images of BIL1-GFP in root cells of 4-day-old seedlings grown on medium in the wild-type (WT) and BSS1-OX2 backgrounds after treatment with 3 μM Brz for 3 hours (scale bar: 10 μm).
FIG. 9D shows the ratio of the nuclear signal intensity to cytosolic signal intensity in the root cells of 4-day-old wild-type (WT) and BSS1-OX2 seedlings. The results are presented as the mean±s.d. (n=27, *P<0.01, Student's t-test).

The images were analyzed using ImageJ software. To measure the ratio of the nuclear and cytosolic signals of BIL1-GFP for each cell, the signal intensities in the nucleus and cytosol were calculated from the mean of the intensity in each area. The nuclear to cytosolic signal ratio was then calculated for each cell. The average nuclear/cytosolic signal ratio and standard error were calculated from measurements of at least 54 cells from each line (FIG. 9B). Line scan measurements from the vacuole to the nucleus through the cytosol were performed, and representative plot profiles of sample measurements are presented in FIG. 5C.

(9) BiFC

The BSS1, BIL1, and BES1 cDNA were amplified using the BSS1-Forward and BSS1-Reverse-SC 5'-CTA-GAAATGGTGGTGGTGGTGATGATAC-3' (SEQ ID NO: 27) primers for BSS1, the BIL1-Forward and BIL1-Reverse primers for BIL1, and the BES1-Forward 5'-CACCAT-GACGTCTGACGGAGCAAC-3' (SEQ ID NO: 28) and BES1-Reverse 5'-ACTATGAGCTTTACCATTTCCAAG-3' (SEQ ID NO: 29) primers for BES1, cloned into pENTR/D-TOPO (Invitrogen), and subsequently cloned into the binary Gateway expression vectors nEYFP/pUGW0 and cEYFP/pUGW2 by LR recombination. The resulting vectors encoding nEYFP-BSS1 and nEYFP-BIL1 or BES1-cEYFP were used for a transient expression analysis in *Arabidopsis* suspension-cultured cells as previously described (Ueda et al., 2004, Functional differentiation of endosomes in *Arabidopsis* cells, Plant J. 40: 783-789). The protoplasts were observed using an LSM700 microscope (Zeiss).

(10) Immunoblot Analysis

Light-grown 7- and 10-day-old wild-type, bss1-1D, BSS1-OX, bop1-3 and bop1-3 bop2-1 seedlings were ground in liquid nitrogen and extracted by boiling with equal volumes/fresh weight of 1× Laemmli buffer [50 mM Tris-HCl (pH 6.8), 100 mM DTT, 2% (w/v) SDS, 0.1% (w/v) bromophenol blue, and 10% (w/v) glycerol] for immunoblot analysis of BIL1 and BSS1-GFP. The proteins were separated by SDS-PAGE (10% acrylamide gel). After electrophoresis, the proteins were electrophoretically transferred to a Hybond ECL nitrocellulose membrane (Amersham).

After blocking in TBS (20 mM Tris, 0.137 M NaCl, pH 7.4, and 0.05% polyoxyethylene sorbitol monolaurate) containing 5% non-fat milk (Morinaga milk) at room temperature, the membrane was incubated overnight at 4° C. in Western Blot Immuno Booster Solution 1 (Takara) with a polyclonal antibody (1:20000) against GFP (Molecular Probes) and BIL1 After washing in TBS containing 1% non-fat milk (Morinaga milk) at room temperature, the blots were incubated in Western Blot Immuno Booster Solution 2 (Takara) with a horseradish peroxidase-conjugated secondary antibody (1:50000) (Promega) for 1 h at room temperature, and the complexes were visualized with ECL Immobilon Western HRP substrate (Millipore). The polyclonal antibody against BIL1 was produced by immunizing rabbits with maltose-binding protein (MBP)-tagged BIL1 proteins (91-336 aa). The antibody was affinity purified using a BIL1 polypeptide. The LAS-4000 mini (Fuji Film) digital imaging system was used for detection. A non-reduction immunoblot analysis was performed essentially as previously described (Mou et al., 2003, Inducers of plant systemic acquired resistance regulate NPR1 function through redox changes, Cell 113: 935-944). The images were analyzed using ImageQuant TL software (version 7.0; GE Healthcare Life Sciences) to determine the relative signal intensity.

(11) Precipitation and Surfactant Treatment of the BSS1 Protein Complex

A total of 2 g of plant material was frozen in liquid nitrogen, extracted by grinding with a mortar and pestle and suspended in 5 ml of cold extraction buffer (50 mM Tris-HCl, pH 7.5, 20% sucrose and protease inhibitor cocktail (Sigma)). This lysate was centrifuged at 200 g for 2 min at 4° C., and the resulting supernatant was further centrifuged at 50,000 rpm (153,000×g) for 2 h at 4° C. The pellets were then suspended in 300 μl extraction buffer containing 0.5% surfactant (w/v for CHAPS; v/v for TritonX-100 and Nonidet P-40). The surfactant-treated pellets were centrifuged at 50,000 rpm (153,000×g) for 2 h at 4° C. Each supernatant sample was loaded onto an Amicon Ultra-0.5 Centrifugal Filter (Millipore) and concentrated to a volume of 120 μl. The recovered supernatants and pellets that were extracted from equal volumes of plant material were used for immunoblot analysis.

(12) Yeast Two-Hybrid Analysis cDNA encoding BIL1 without the first 21 amino acids and cDNA encoding BES1 without the first 20 amino acids were cloned into the pDEST32 bait vector (Invitrogen). cDNA encoding full-length BSS1 was cloned into the pDEST22 prey vector (Invitrogen). The resulting plasmids were transformed into the yeast Y187 strain (Clontech). The obtained yeast cells were used for yeast two-hybrid analysis. The positive transformants that grew on the selection medium were further grown and resuspended in assay buffer (180 mM HEPES, 154 mM NaCl, 1 mM L-aspartate (hemi-Mg salt), 1% BSA, and 0.05% Tween 20, pH 7.3) containing 2.23 mM chlorophenol red-β-D-galactopyranoside (CPRG) as a substrate as described in the manufacturer's protocol for the ProQuest Two-hybrid System (Invitrogen). To quantify the protein-protein interaction, the β-galactosidase activity was measured at $OD_{574}$ using a Microplate Reader SH-9000 (CORONA electric), and the β-galactosidase activity was calculated using the following formula: $1000 \times OD_{574}/(OD_{600} \times$ assay time (min)$\times$assay volume (mL)).

(13) Immunoprecipitation Analysis

Plants (5 g fresh weight) grown for 23 days on ½ MS medium were frozen in liquid nitrogen, extracted by grinding with mortar and pestle, and added to 14 mL of cold extraction buffer (50 mM Tris-HCl (pH 7.5), 150 mM NaCl, 5 mM EDTA, 0.1% Triton X-100, 0.2% Nonidet P-40, and protease inhibitor cocktail (Sigma)). This lysate was centrifuged twice at 10,000 g for 5 min at 4° C. The supernatant was incubated for 1 h at 4° C. with anti-FLAG M2 affinity gel (Sigma-Aldrich). The beads were collected and washed four times with ice-cold extraction buffer, and the FLAG-associated proteins were eluted with 2×SDS sample loading buffer (4% SDS, 100 mM Tris-HCl (pH 6.8), 200 mM DTT, 20% glycerol and 0.003% [w/v] BPB). After incubation at 100° C. for 5 minutes, the proteins were resolved by SDS-PAGE. The immunoprecipitated proteins were detected by immunoblot analysis on Hybond ECL nitrocellulose membranes (GE Healthcare) using a monoclonal anti-Flag M2 antibody (Sigma-Aldrich) at a 1:500 dilution and an anti-GFP antibody (Molecular Probes) at a 1:2000 dilution.

(14) Accession Number

Sequence data described herein have been registered with the accession numbers shown below in the *Arabidopsis*

Genome Initiative or GenBank/EMBL data library: BSS1 (AT3G57130), BIL1 (AT1G75080), BES1 (AT1G19350), BRI1 (AT4G39400), DWF4 (AT3G50660), DET2 (AT2G38050), BIN2 (AT4G18710), 14-3-3 (AT1G22230), SAUR-AC1 (AT4G38850), TCH4 (AT4G57560), CPD (AT5G05690), ACT2 (AT3G18780), AS2 (AT1G65620), AP1 (AT1G69120), Pp-BOP1 (Phypa_119190), Pp-BOP2 (Phypa_121620), NPR1 (AT1G64280), BZS (AT4G39070), LOB (AT5G63090), CUC (AT3G15170), and AHA1 (AT2G18960).

[Results]

(Example 1) Identification of the Causative Gene for the Bss1-1D Mutant

To search for novel factors involved in BR signaling, approximately 10,000 *Arabidopsis thaliana* activation-tagged lines (Nakazawa et al., 2003, Activation tagging, a novel tool to dissect the functions of a gene family, Plant J. 34: 741-750) were screened using Brz. As a result, Brz-sensitive-short hypocotyl 1-1D (bss1-1D) was isolated. The bss1-1D mutant had a shorter hypocotyl than that of the wild-type plant when grown in the dark on medium with Brz, although bss1-1D showed a normally elongated hypocotyl in the absence of Brz (FIGS. 1A and 1B and FIGS. 12D and 12E).

Light-grown bss1-1D mutants presented phenotypes similar to those of the BR biosynthesis- and signaling-defective mutants det2, bri1, and bin2 (FIGS. 1C and 1D and FIGS. 12A to 12C). These phenotypes of bss1-1D suggest that BR signaling is suppressed in bss1-1D mutants.

To identify the bss1-1D mutation, we analyzed the co-segregation of the Brz-sensitive-short hypocotyl phenotype and found a T-DNA insertion site at the end of chromosome III. The expression of the At3g57130 gene, which is located approximately 1 kb upstream of the T-DNA insertion, was increased in the bss1-1D mutant compared to that of the wild type, as determined by quantitative real time-PCR (qRT-PCR) (FIGS. 1E and 1F). To confirm that the hyperexpression of this gene caused the bss1-1D phenotype, we generated plants overexpressing At3g57130 (FIG. 1F). The BSS1-overexpressing plant (BSS1-OX) exhibited short hypocotyls when grown in the dark on medium containing Brz and a dwarf phenotype when grown in light, similar to bss1-1D (FIGS. 1A to 1D). Therefore, At3g57130 was identified as BSS1.

Figure 13:
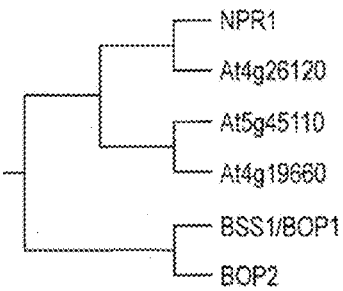
FIG. 13A shows the multiple sequence alignments of BSS1/BOP1 (SEQ ID NO: 32), BOP2 (SEQ ID NO: 33), and NPR1 (SEQ ID NO: 34) proteins.
FIG. 13B shows the phylogenetic trees of BSS1/BOP1 and its homolog.

BSS1 encodes a BTB-POZ domain protein with ankyrin repeats known as BLADE ON PETIOLE 1 (BOP1), which plays an important role in regulating leaf morphogenesis, leaf patterning, and floral abscission. BOP1 belongs to a family of proteins that includes the plant defense response regulator NPR1 (FIGS. 13A and 13B).

(Example 2) Elucidation of the Mechanism of BR Signaling Regulation by BSS1

To determine whether the BR-deficient phenotype was due to the inhibition of BR signaling, expression of BR-responsive genes (TCH4, BAS1, IAA19, and SAUR-AC1) was analyzed by qRT-PCR. The expression of TCH4, BAS1, IAA19, and SAUR-AC1 was increased by active BR brassinolide (BL) and suppressed by Brz in wild-type (WT) plants. In BSS1-OX, expression of TCH4, BAS1, IAA19, and SAUR-AC1 was remarkably reduced under control (Mock) conditions compared to that of the wild-type plant. The suppression ratio of gene expression in BSS1-OX was enhanced in the presence of Brz (FIG. 2A).

The phosphorylation status of a downstream biochemical marker, BIL1 which is highly phosphorylated under low-BR conditions and dephosphorylated by BR treatment, was analyzed. The amounts of phosphorylated BIL1 and dephosphorylated BIL1 decreased in bss1-1D and BSS1-OX plants, respectively, compared with the levels in wild-type plants (FIG. 2B). These results indicate that BR signaling in bss1-1D and BSS1-OX is suppressed upstream of BIL1.

Figure 3:
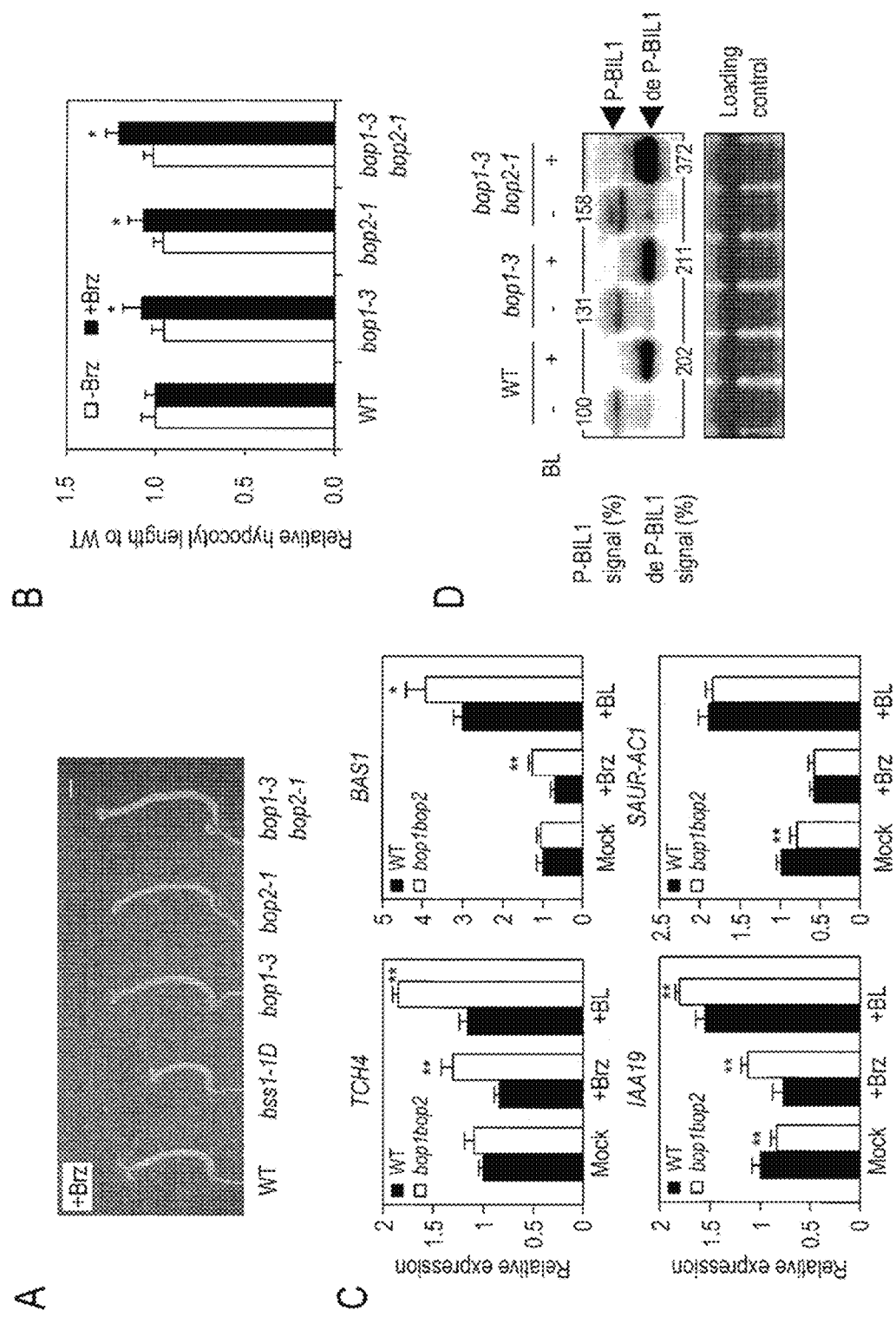
FIG. 3A shows phenotypes of wild-type (WT), bss1-1D, and BSS1-deficient mutants (bop1-3, bop2-1, and bop1-3 bop2-1) grown in the dark for 7 days on medium containing DMSO or 3 μM Brz (scale bar: 1 mm).
FIG. 3B shows relative hypocotyl length of BSS1-deficient mutants (bop1-3, bop2-1, and bop1-3 bop2-1) compared with wild-type (WT) on medium containing DMSO or 3 μM Brz after growth in the dark for 7 days. The results are presented as the mean±s.d. (n=34, *P<0.05, Student's t-test).
FIG. 3C shows Brz and BL responsiveness of BR-regulated genes in the BSS1-deficient mutant (bop1-3 bop2-1). The expression levels of TCH4, BAS1, IAA19, and SAUR-AC1 were analyzed by qRT-PCR in 9-day-old light-germinated seedlings and treated with medium containing DMSO (Mock), 3 μM Brz (+Brz), or 100 nM BL (+BL) for 3 hours. The data represent the mean±s.d. of 4 independent experiments (**P<0.01, *P<0.05, Student's t-test).
FIG. 3D shows immunoblot analysis of BIL1 phosphorylation status of wild-type (WT) and a BSS1-deficient mutant (bop1-3 bop2-1). The signal intensities of phosphorylated BIL1 (above) and dephosphorylated BIL1 (below) are shown by arrowhead, and each band signal is counted as a percentage relative to the level of phosphorylated BIL1 in WT seedlings. The lower panel shows a Ponceau S-stained gel.

Single and double T-DNA insertion mutants in the promoter region, bop1-3, bop2-1, and bop1-3 bop2-1, exhibited modestly but significantly ($P<0.05$) longer hypocotyls than those of the wild type when grown in the dark on medium with Brz (FIGS. 3A and 3B). In the bop1-3 bop2-1 mutant, expression of TCH4, BAS1 and IAA19 was remarkably enhanced in the presence of BL compared to that of the wild-type plant (FIG. 3C). Immunoblot analysis indicated that the amounts of phosphorylated BIL1 and dephosphorylated BIL1 increased in bop1-3 and bop1-3 bop2-1 plants, respectively (FIG. 3D). These results suggest that the loss of BSS1 activates BR signaling.

Figure 4:
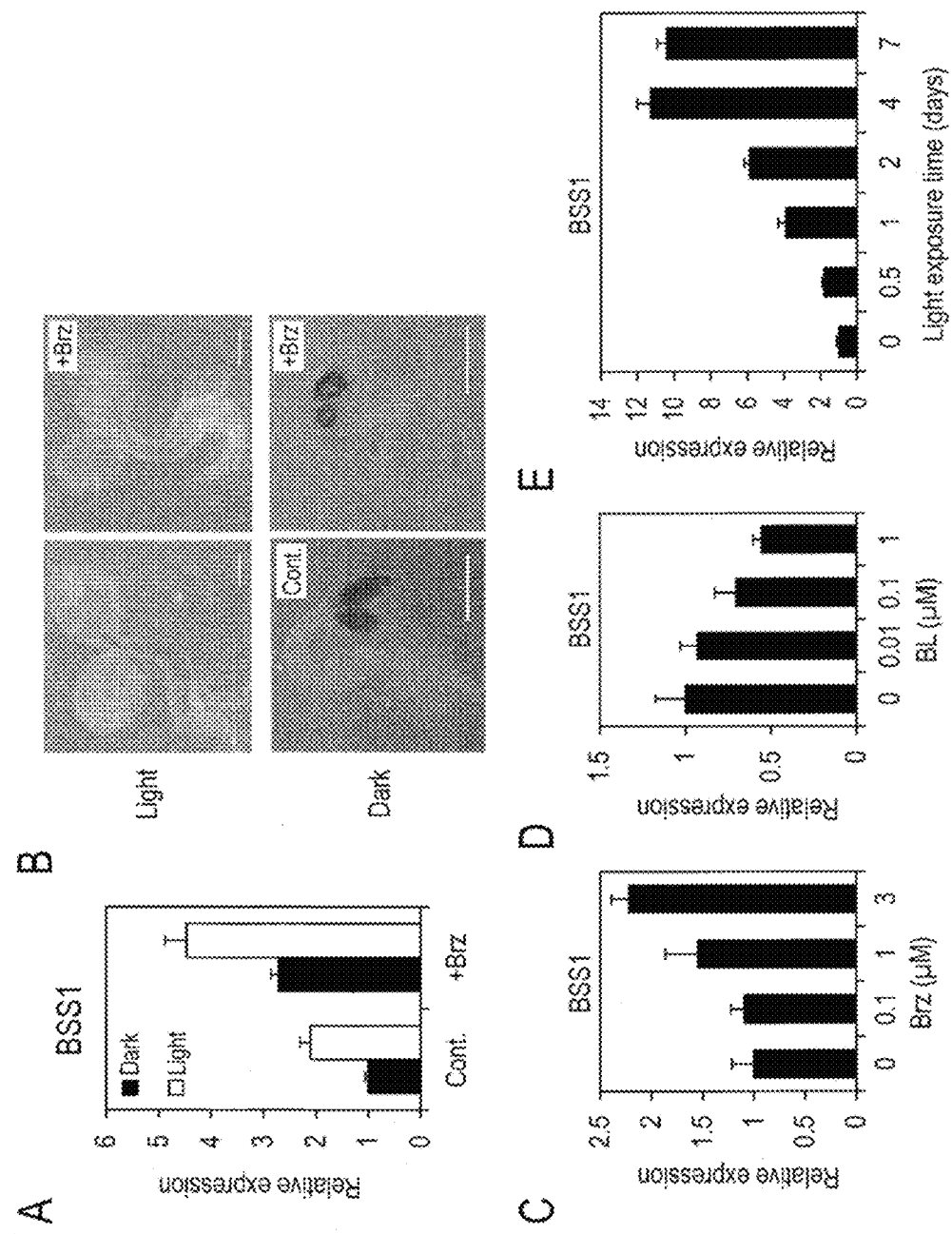
FIG. 4A shows the results of qRT-PCR analysis of the expression levels of BSS1 in wild-type (WT) seedlings grown on medium without (cont.) or with 3 μM Brz (+Brz) in the dark or light for 7 days. The data represent the mean±s.d. from 4 independent experiments.
FIG. 4B shows GUS reporter gene expression in the transgenic plant expressing BSS1 pro:GUS. The samples were grown in the same conditions as FIG. 4A for 3 days (scale bar: 5 mm).
FIGS. 4C to 4E show the results of determining the BSS1 expression level by qRT-PCR. Wild-type (WT) seedlings grown on medium with different concentrations of Brz (FIG. 4C) and BL (FIG. 4D) in the light for 7 days and dark-grown seedlings exposed to light for 0-7 days (Figure E) were used for analysis of the BSS1 expression level. The data represent the mean±s.d. of 4 independent experiments.

The BR-regulated expression of BSS1 was examined in more detail by qPCR analysis. As a result, BSS1 expression increased in response to the dose-dependent addition of Brz during early germination (FIGS. 4A and 4C). By contrast, BSS1 expression decreased in response to BL (FIG. 4D).

The analysis of transgenic plants with the BSS1 promoter region that was fused to the β-glucuronidase gene (BSS1 pro: GUS) exhibited strong expression in light-grown seedlings but not in dark-grown seedlings. Brz caused BSS1 expression in the hypocotyls in the dark and in the cotyledons under light and dark conditions (FIG. 4B). BSS1 expression was induced by the deficiency of BR with Brz treatment and was suppressed by light and in seedlings (FIG. 4E). These results suggest that BSS1 regulates the optimum length of hypocotyl elongation via the down-regulation of BR signaling during early germination. Therefore, BSS1 plays important roles not only in leaf morphogenesis but also in hypocotyl growth through BR signaling.

Figure 5:
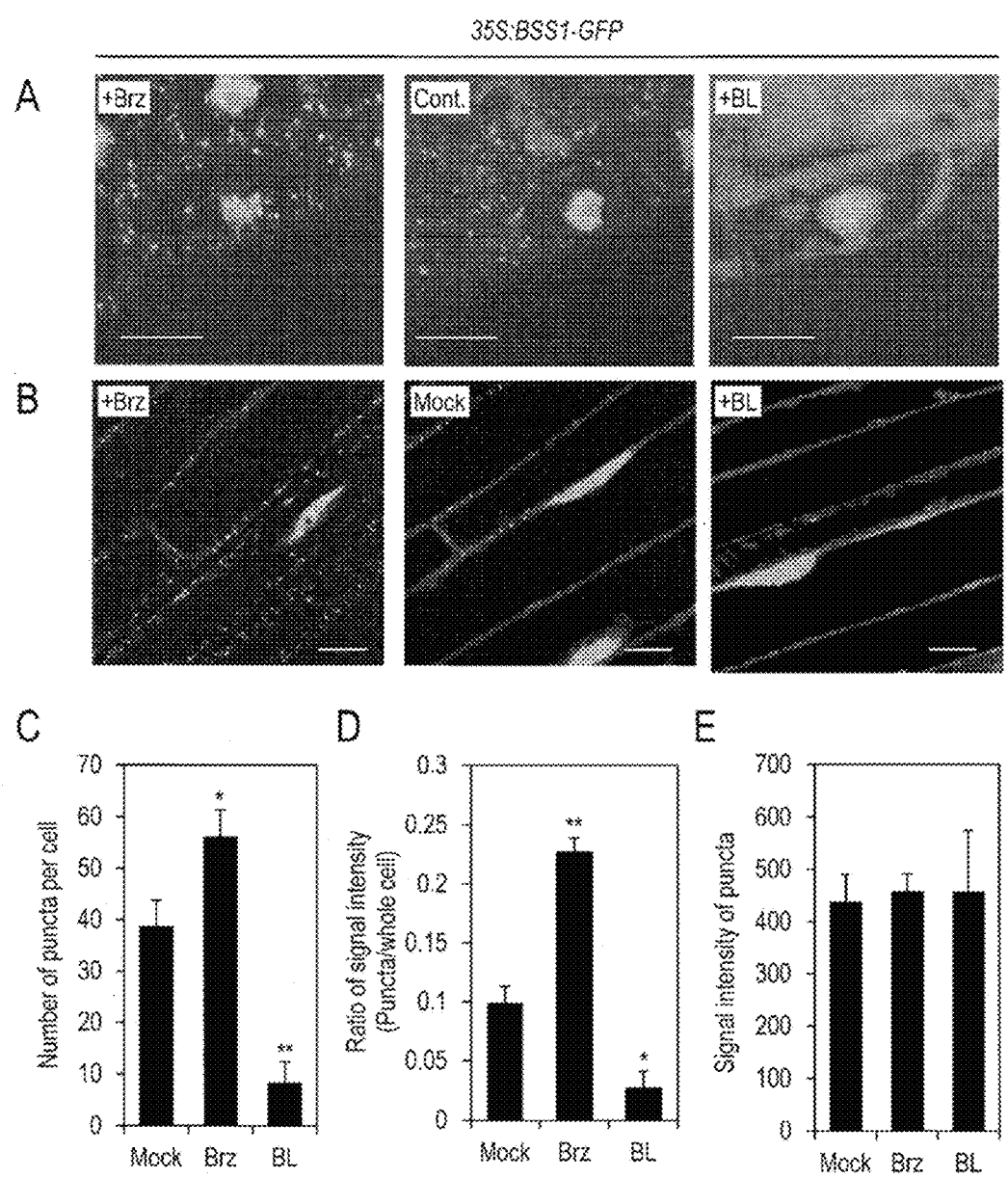
FIG. 5A shows BSS1-GFP in root cells of 10-day-old seedlings grown on medium with 3 μM Brz (left) or 100 nM BL (right) (scale bar: 10 μm; Cont.: mock-treated control).
FIG. 5B shows BSS1-GFP in hypocotyl cells of 4-day-old seedlings grown in the dark that were treated with 3 μM Brz (+Brz), the same amount of DMSO as mock treatment (Mock), or 100 μM BL (+BL) for 1 hour (scale bar: 10 μm).
FIGS. 5C to 5E show analysis of BSS1-GFP puncta signal intensities upon treatment with Brz and BL. Seven-day-old BSS1-GFP transgenic seedlings were treated for 3 hours with 3 μM Brz (Brz), an equal volume of DMSO (Mock), or 100 μM BL (BL). The graph in FIG. 5C shows the number of puncta per cell. The graph in FIG. 5D shows the ratio of puncta signal intensity compared with the whole-cell intensity (n=9, *P<0.05, **P<0.01, Student's t-test). The graph in FIG. 5E shows the puncta signal intensity (n=73). The results are represented as the mean±s.d. The signal intensity was measured using ImageJ software.

(Example 3) Subcellular Localization of BSS1 and Characteristics of Punctuate BSS1 Structures The subcellular localization of BSS1 was examined. In the CaMV 35S:BSS1-GFP transformant, which had a shorter hypocotyl under Brz conditions and a shorter inflorescence compared to those of the wild-type plant, BSS1-GFP localized to both the nucleus and cytosol. Many punctuate BSS1-GFP signals with diffuse signal were observed mainly in the cytosol (FIG. 5A). Interestingly, in seedlings grown on medium containing Brz, the punctate BSS1-GFP increased in number, and the diffused BSS1-GFP signal in the cytosol was reduced compared to that under the control conditions. By contrast, on medium with BR, the punctate BSS1-GFP decreased in number and diffused in the cytosol. Such responsiveness of punctate BSS1-GFP to BR and Brz began 15 minutes after treatment and was observed in both the roots (FIG. 5A) and hypocotyls (FIG. 5B). Treatment with Brz increased the number of intense puncta and decreased the cytosolic fluorescence signal compared to those of the mock treatment. Treatment with BL decreased the number of intense puncta (FIG. 5C). Brz treatment caused an increase in the fluorescence intensity of the puncta per cell with respect to the whole-cell fluorescence intensity (FIG. 5D), but the single fluorescence intensity of each punctum was not different between the Brz and BL treatment conditions (FIG. 5E). These results suggest that the formation of punctate BSS1 is caused by Brz and that its dissociation is caused by BR.

FM4-64 stains cellular membranes and endocytic structures, which are observed as punctate structures. Brefeldin A (BFA) inhibits early endosomes and the Golgi apparatus, which appear as punctate cytosolic organelles.

To determine whether the punctate BSS1-GFP fluorescence signals were from these cellular organelles or protein complex, the BSS1-GFP signal after treatment with FM4-64 (FIG. 6B) and BFA (FIG. 6C) was analyzed. The punctate BSS1 did not merge with FM4-64, and their formation was not inhibited by BFA. These results suggest that the puncta were neither endosomes nor the Golgi apparatus.

Figure 6:
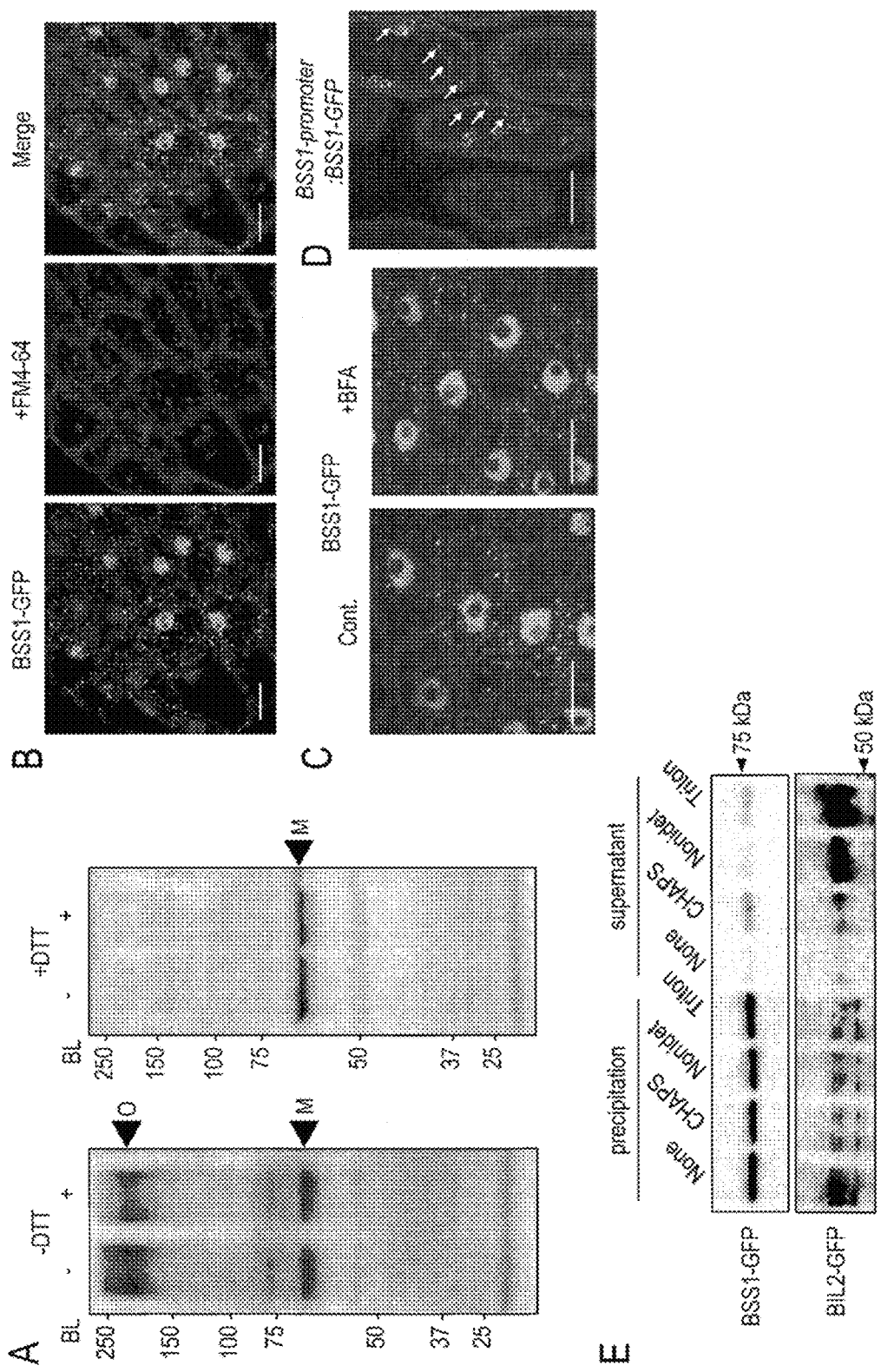
FIG. 6A shows the analysis results of immunoblotting of non-reduced (−DTT) and reduced (+DTT) proteins from the plant leaf by using an anti-GFP antibody in transgenic plants grown on medium with Brz for 10 days. Oligomeric BSS1-GFP and monomeric BSS1-GFP are shown by arrowhead O and arrowhead M, respectively.
FIG. 6B shows the root cells of BSS1-GFP transgenic plants stained with 4 μM FM4-64 for 30 minutes (scale bar: 10 μm).
FIG. 6C shows the root cells of BSS1-GFP transgenic plants treated with 50 μM brefeldin A (BFA) for 1 hour (scale bar: 10 μm).
FIG. 6D shows the hypocotyl cells of BSS1-promoter:BSS1-GFP transgenic plants grown for 4 days on medium with 3 μM Brz (white arrowhead: BBS1-GFP puncta; scale bar: 10 μm).
FIG. 6E shows effects of ultracentrifugation and surfactant treatment on BSS1 oligomers. Total lysates were prepared from the transgenic plants and ultracentrifuged to separate the insoluble (precipitation) and soluble (supernatant) fractions. The insoluble fractions were then treated with the indicated surfactants and subjected to further ultracentrifugation. The resulting supernatants and pellets were analyzed by immunoblotting. As a control, the indicated surfactant-treated BIL2-GFP (protein localized to the mitochondria) samples were centrifuged as above.

Furthermore, punctate BSS1 could be observed in both the CaMV 35S promoter::BSS1-GFP transformant and the BSS1 promoter::BSS1-GFP transformant (FIG. 6D). These analyses showed that BSS1 naturally formed puncta.

To determine whether punctate BSS1 is formed by a protein oligomer, a non-reducing immunoblot analysis was performed. Under non-reducing conditions (without DTT), two bands representing the monomeric BSS1-GFP fusion protein (molecular weight: 78,000) and a much higher-molecular-weight protein were detected (FIG. 6A, arrowhead O). The higher-molecular-weight protein signal was lost under reducing conditions (with DTT), whereas that of the monomeric BSS1 signal remained (FIG. 6A, arrowhead M). Although BOP1 forms a homodimer (Jun et al., 2010, BLADE-ON-PETIOLE1 coordinates organ determinacy and axial polarity in Arabidopsis by directly activating ASYMMETRIC LEAVES2, Plant Cell 22: 62-76), the detected high-molecular-weight signal was an oligomer of BSS1. After BL treatment, the amount of the oligomeric form of BSS1-GFP significantly decreased.

Further biochemical analyses were performed to enable a more detailed characterization of punctate BSS1 structures. Given that large protein complexes and cellular organelles can be precipitated by ultracentrifugation, ultracentrifugation was performed using protein extracts from BSS1-GFP transformants and mitochondrial protein BIL2-GFP transformants (Davka et al., 2013), which both present punctate GFP fluorescence signals in the cytosol. Pellets from the first ultracentrifugation were treated with the surfactants CHAPS, Nonidet P-40 or TritonX-100. These surfactant treatments solubilize organelle membranes but not protein complexes (Nishikoori et al., 2006; Kinoshita et al., 2005, Binding of brassinosteroids to the extracellular domain of plant receptor kinase BRI1, Nature 433: 167-171). After a second ultracentrifugation with the surfactant-treated fractions, the BIL2-GFP signals were stronger in the pellet and weaker in the supernatant compared with buffer-treated (no surfactant) control fractions. Nevertheless, the BSS1-GFP signals were similarly strong in the pellets after treatment both with and without surfactant. The BSS1-GFP signals were very weak in all of the supernatant fractions and were increased by surfactant treatment (FIG. 6E). These results suggested that the punctate fluorescence signals observed in BSS1-GFP transformants were indicative of protein complexes and were not the result of monomeric proteins being packaged inside organelle membranes, as detected in the BIL2-GFP transformants. The BSS1 puncta are linked by disulfide bonds between each BSS1 unit, and this complex is dissolved by BL and assembled by Brz.

Figure 7:
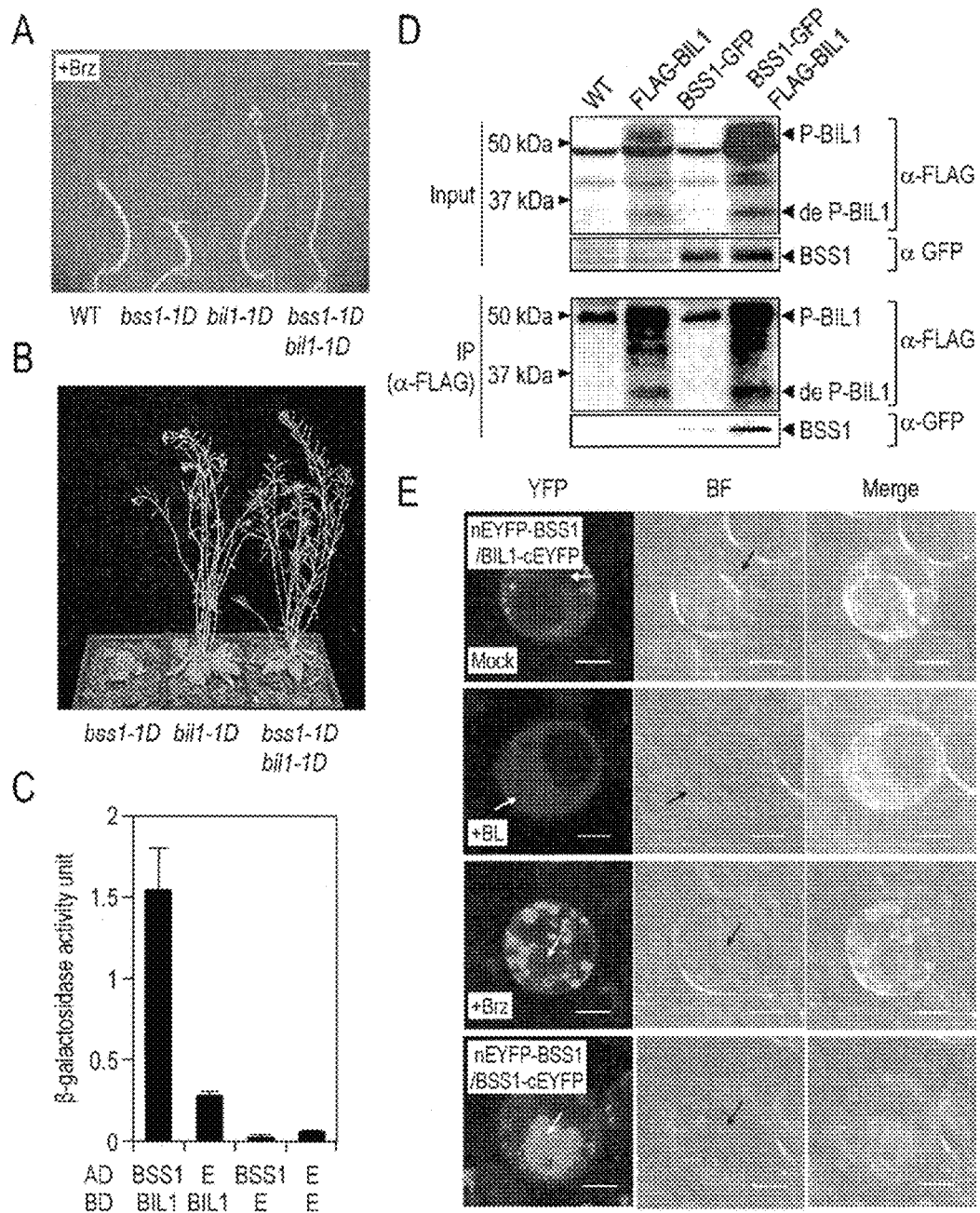
FIG. 7A shows the phenotypes of the wild type (WT), bss1-1D, bil1-1D, and bss1-1D bil1-1D double mutant grown on medium containing 3 μM Brz in the dark for 7 days (scale bar: 1 mm).
FIG. 7B shows phenotypes of bss1-1D, bil1-1D, and the bss1-1D bil1-1D double mutant grown in soil in long-day conditions for 40 days.
FIG. 7C shows the results of yeast two-hybrid assay between BSS1 and BIL1 based on measuring β-galactosidase activity. BIL1 was fused with the binding-domain (BD) and BSS1 was fused with the prey domain (AD). Empty vector (E) was used as a control. The results are presented as the mean±s.d. from 3 independent experiments.
FIG. 7D shows the results of co-immunoprecipitation of BSS1 and BIL1 The seedlings of wild-type (WT), FLAG-BIL1 BSS1-GFP, and BSS1-GFP FLAG-BIL1 were grown on plates under light for 23 days. FLAG-BIL1 was immunoprecipitated using an anti-FLAG antibody and immunoblotted using anti-GFP and anti-FLAG antibodies.
FIG. 7E shows the results of bi-molecular Fluorescence Complementation (BiFC) analysis of the interaction between BSS1 (nEYFP-BSS1) and BIL1 (BIL1-cEYFP) in Arabidopsis protoplast cells. The protoplast medium contained DMSO, 100 nM BL, or 3 μM Brz and cells were cultured for 12 hours. The bottom panels show protoplasts cotransfected with nYFP-BSS1 and BSS1-cEYFP (YFP: YFP fluorescence; BF: bright field; Merge: merged image of YFP and BF; arrow: nucleus; scale bar: 5 μm).

(Example 4) Elucidation of the Mechanism of Transport of BIL1 from the Cytosol to the Nucleus by the BSS1 Protein Complex To investigate the possible function of the punctate BSS1 in BR signaling, the genetic interaction between bil1-1D and bss1-1D was analyzed. bss1-1D and bil1-1D double mutants presented similar phenotypes to that of bil1-1D (FIGS. 7A and 7B). These results indicated that bil1-1D is epistatic to bss1-1D and that BIL1 acts downstream of BSS1.

To detect a direct interaction between BSS1 and BIL1, a yeast two-hybrid assay was performed (FIG. 7C). The cDNA of BIL1 was cloned into the pDEST32 binding-domain vector (BD). The cDNA of BSS1 was cloned into the pDEST22 prey vector (AD). In the yeast transformed by pBD-BIL1 and pAD-BSS1, a higher β-galactosidase activity was detected compared to that of the yeast with only one vector. These results suggest that BSS1 and BIL1 can directly interact with each other biochemically.

The BIL1-FLAG protein was immunoprecipitated by anti-FLAG antibodies in transgenic Arabidopsis plants expressing both BSS1-GFP and BIL1-FLAG, and the resulting immunoprecipitates were analyzed by immunoblot analysis with anti-FLAG and anti-GFP antibodies. The anti-FLAG antibody immunoprecipitated BIL1-FLAG and coimmunoprecipitated BSS1-GFP, whereas no BSS1-GFP signal was detected using the immunoprecipitates of the transformants expressing BSS1-GFP alone or wild-type Arabidopsis (FIG. 7D).

Both phosphorylated BIL1-FLAG and dephosphorylated BIL1-FLAG were detected by immunoblotting, and the ratio of dephosphorylated BIL1-FLAG to phosphorylated BIL1-FLAG in the input fraction was not altered after immunoprecipitation (FIG. 7D). The results of these experiments strongly suggest that BSS1 interacts with BIL1 in plants.

To analyze the direct interaction between BSS1 and BIL1 in the plant cell and to identify the localization of the possible interaction between the two proteins, a bi-molecular fluorescence complementation (BiFC) analysis was performed. Arabidopsis protoplast cells were cotransformed with nEYFP-BSS1 and/or BIL1-cEYFP constructs. The protoplast cells were treated with medium containing DMSO, 100 nM BL, or 3 μM Brz for 12 hours. The YFP fluorescence signal caused by the binding of nYFP-BSS1 and BIL1-cYFP was only observed in the cytosol and not in the nucleus of the Arabidopsis protoplasts (FIG. 7E). The punctate YFP signal increased with Brz treatment. These puncta caused by Brz were interestingly only detected in the cytosol and not in the nucleus (FIG. 7E). These results suggest that the complex of BSS1 remained in the cytosol, and the BSS1 protein complex restricted BIL1 to the cytosol.

After BL treatment, the YFP signal resulting from the interaction between nYFP-BSS1 and BIL1-cYFP was diffuse and spread throughout the cytosol and the nucleus (FIG. 7E). The diffuse BSS1 only dimerized with BIL1 The diffuse BSS1 did not restrict BIL1 to the cytosol, and BIL1 could be imported into the nucleus under BL-treated conditions.

A YFP signal caused by the dimerization with nYFP-BSS1 and BSS1-cYFP was observed in the cytosol, and these signals could in some cases be detected as puncta in the nucleus (FIG. 7E). These results suggest that the fluorescence signal from BSS1-GFP in the nucleus after Brz treatment (FIG. 5A) is caused by BSS1 itself and not by the BSS1-BIL1 complex.

Figure 8:
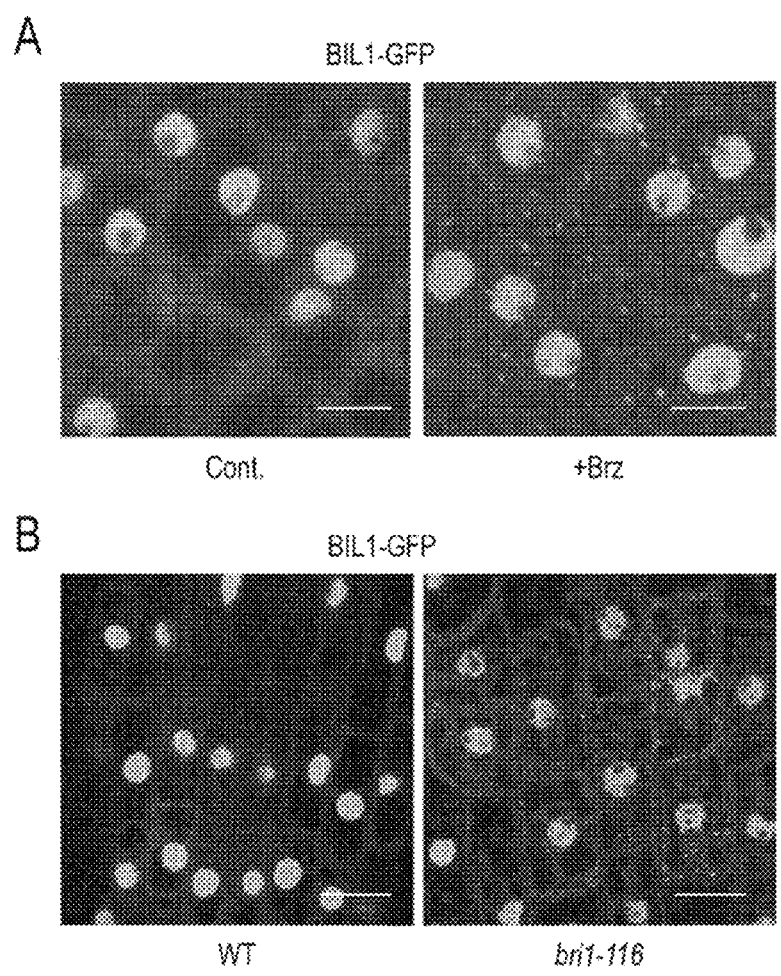
FIG. 8A shows BIL1-GFP in root cells of 4-day-old seedlings grown on medium with 3 μM Brz (+Brz) or DMSO (Cont.) (scale bar: 10 μm).
FIG. 8B shows BIL1-GFP in root cells of 4-day-old seedlings in the wild-type (WT) or bri1-116 background grown in the dark (scale bar: 10 μm).

BIL1-GFP was reported to localize to both the cytosol and nucleus in its diffuse form (Ryu et al., 2007, Nucleocytosolic shuttling of BZR1 mediated by phosphorylation is essential in Arabidopsis brassinosteroid signaling, Plant Cell 19: 2749-2762). However, many punctate BIL1-GFP signals in the cytosol after Brz treatment (FIG. 8A) and in the bri1-116 mutant background (FIG. 8B) were detected. These results suggest that BSS1 and BIL1 naturally form puncta in the cytosol under BR-deficient conditions.

Figure 10:
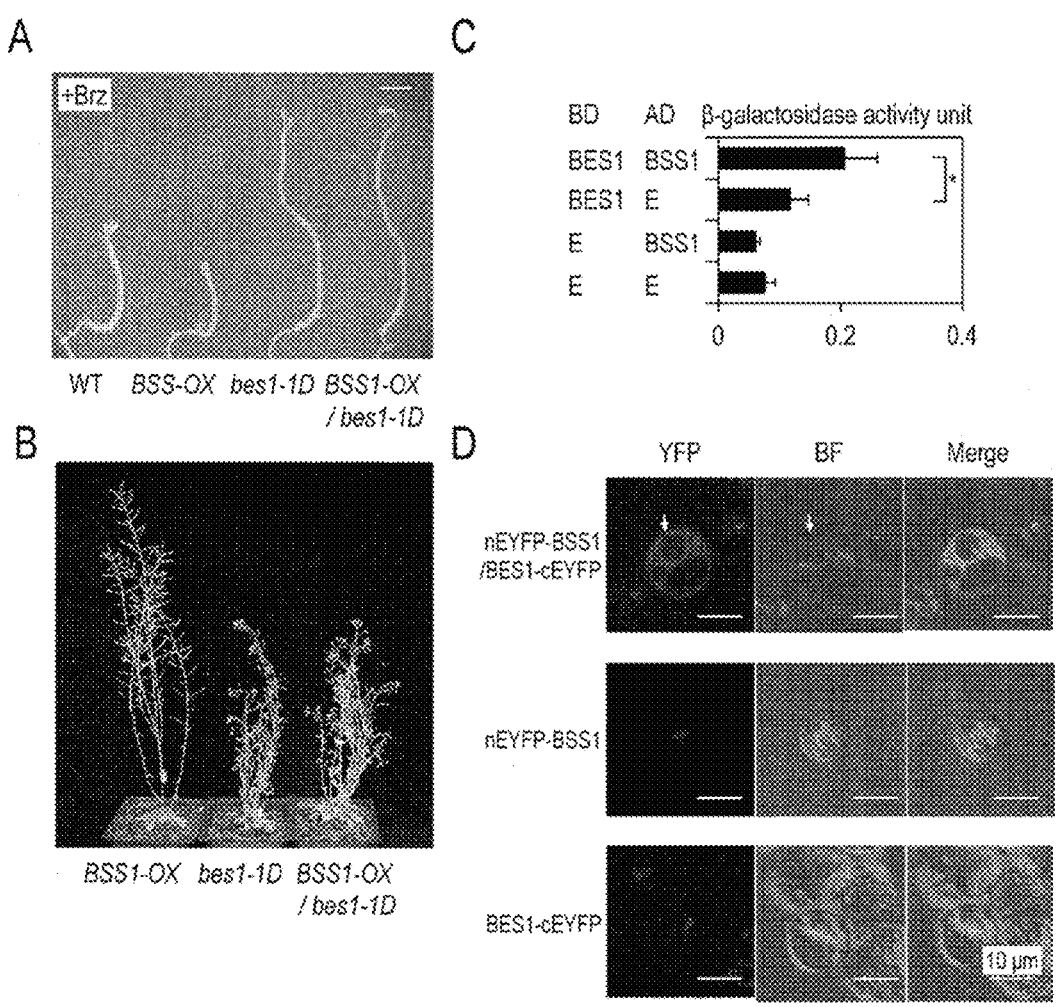
FIG. 10A shows phenotypes of wild-type (WT), BSS1-OX, bes1-1D, and BSS1-OX/bes1-1D double mutant grown on medium containing 3 μM Brz in the dark for 7 days (scale bar: 1 mm).
FIG. 10B shows phenotypes of BSS1-OX, bes1-1D, and BSS1-OX/bes1-1D double mutant grown in soil under long-day conditions for 40 days.
FIG. 10C shows the interaction between BSS1 and BES1 using yeast two-hybrid assay, as assessed by measuring β-galactosidase activity. cDNA encoding BES1 without the first 20 amino acids was cloned into the pDEST32 binding domain vector (BD). The cDNA of BSS1 was cloned into the pDEST22 prey vector (AD). Empty vector (E) was used as a control. The results are presented as the mean±s.d. from 3 independent experiments (*P<0.05, Student's t-test).
FIG. 10D shows bi-molecular Fluorescence Complementation (BiFC) analysis of the interaction between BSS1 and BES1 in Arabidopsis protoplast cells. The protoplast cells were cotransfected with nEYFP-BSS1 and/or BES1-cEYFP constructs. The protoplast cells were grown in medium containing DMSO as control experiments (YFP: YFP fluorescence; BF: bright field; Merge: merged image of YFP and BF; arrow: nucleus; scale bar: 5 μm).
Figure 11:
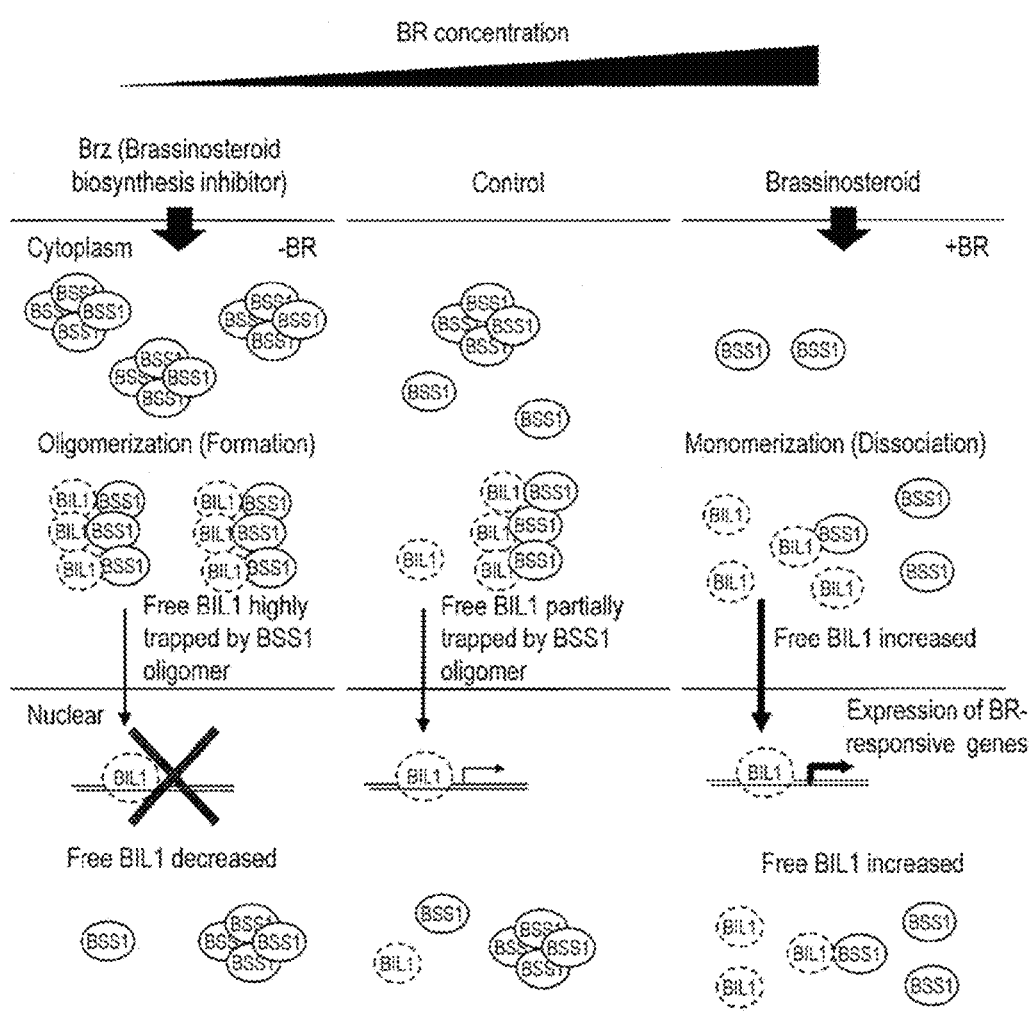
FIG. 11 shows a model of BSS1 function in BR signaling. In the absence of BR activation by Brz, BSS1 mRNA expression was induced. BSS1 forms homo-oligomers and binds to BIL1 preventing the transport of BIL1 to the nucleus. Upon stimulation of BR, the BSS1 oligomer was reduced to a monomer, allowing BIL1 to be transferred to the nucleus and to induce expression of BR-responsive genes.
Figure 12:
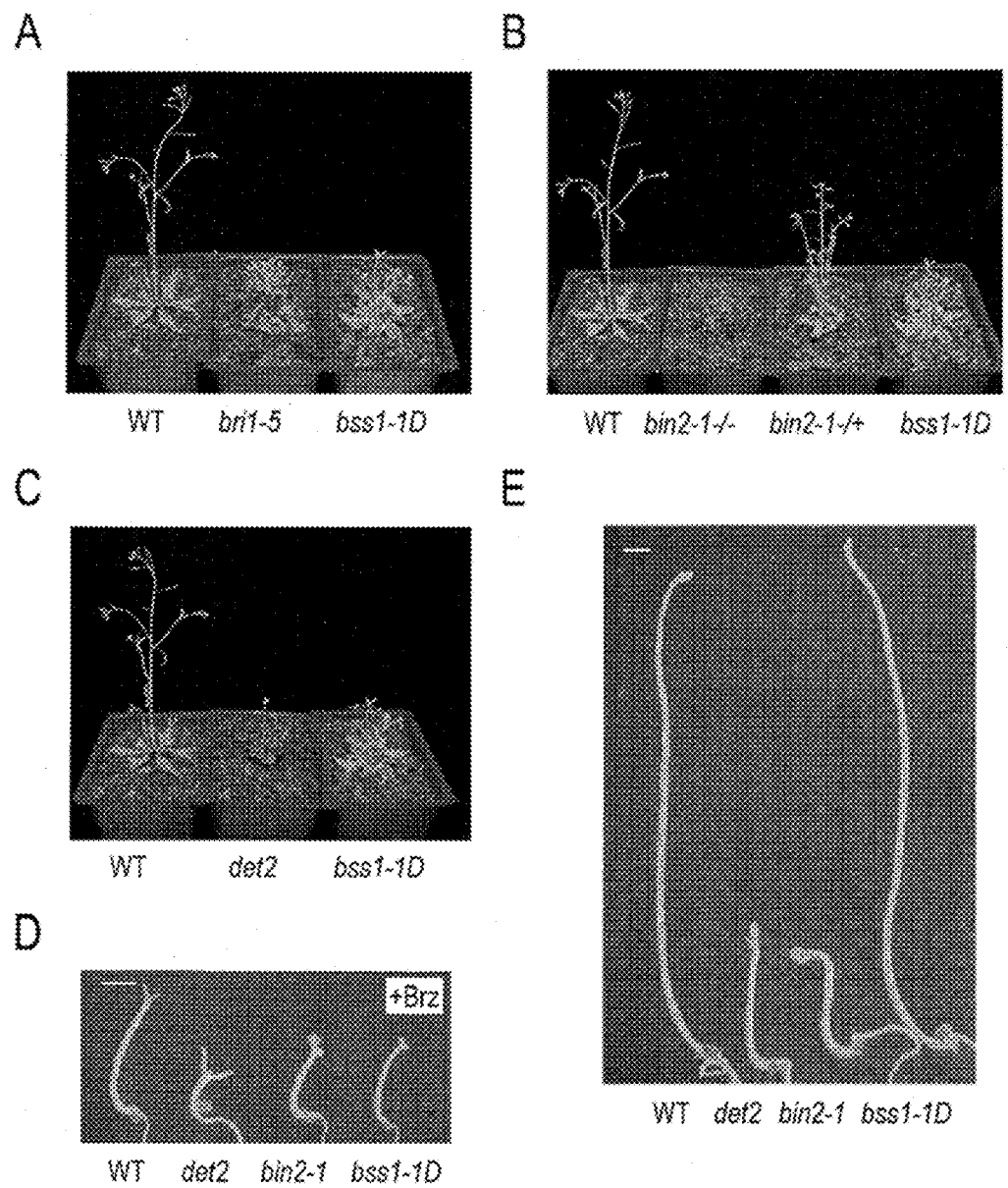
FIGS. 12A to 12C show phenotypes of wild-type (WT), bss1-1D, BR-biosynthesis mutant (det2), and BR-signaling mutant (bri1, bin2) grown in soil in long-day conditions for 35 days.
FIGS. 12D to 12E show phenotypes of wild-type (WT), bss1-1D, and BR-biosynthesis mutant (det2), and BR-signaling mutant (bin2-1) grown on medium with 3 μM Brz (FIG. 12D) or without 3 μM Brz (FIG. 12E) in the dark for 7 days.

To analyze the effect of BSS1 for the transport of BIL1 from the cytosol to the nucleus, the nuclear localization of BIL1 under BSS1-deficient and overexpression conditions was observed and measured. The nuclear-to-cytosolic ratio of the BIL1-GFP signal was higher in the bop1-3 bop2-1 background than in the wild-type background. The fluorescence ratio decreased in the wild-type background upon treatment with Brz, but the enhanced nuclear BIL1-GFP signal in the bop1-3 bop2-1 background was strongly maintained under Brz conditions. Punctate BIL1-GFP signals were observed after Brz treatment in the wild-type background but were not detected in bop1-3 bop2-1 plants treated with Brz. These results suggested that BSS1-deficiency promotes resistance to Brz in the regulation of BIL1-GFP localization and puncta formation (FIGS. 9A and 9B). By contrast, the BIL1-GFP signal in the nucleus was weaker in the BSS1-overexpression transformant background than in the wild-type background (FIGS. 9C and 9D). In both BSS1-deficient and overexpression backgrounds, the BIL1-GFP signal was detected in the nucleus and cytosol. Nevertheless, the BIL1-GFP nucleus/cytosol signal ratio was higher in the bop1-3 bop2-1 background (FIGS. 9A and 9B) and lower in the BSS1-overexpression transformant background (FIGS. 9C and 9D) than in the wild-type background. These results suggest that the binding of BSS1 to BIL1 and the punctate protein complex formation of BSS1 inhibits the transport of BIL1 to the nucleus from the cytosol. Simultaneously, genetic and direct interactions were detected between BSS1 and BES1, which is the homolog of BIL1 (FIG. 10).

(Example 5) Preparation of Rice Transformants

A vector was constructed by inserting the rice BSS1 homologous gene (OsBSS1) into pANDA, which is an RNAi vector, and then, transformation of rice was conducted. At first, cloning of the rice BSS1 homologous gene (OsBSS1) was conducted. Total RNA of the wild-type Nipponbare rice was extracted using an RNA easy plant kit (Qiagen). Next, cDNA was synthesized from the total RNA using a SuperScript III kit (Invitrogen). The resulting cDNA was used as a template to conduct PCR using the following primers, thereby amplifying OsBSS1. OsBSS1-GW-F3: caccatgagctccgaggactcgctcaaatccttgtcg (SEQ ID NO: 30) OsBSS1-GW-R3: ttatgcgaagccattggggaagtacatggcggg (SEQ ID NO: 31)

Figure 14:
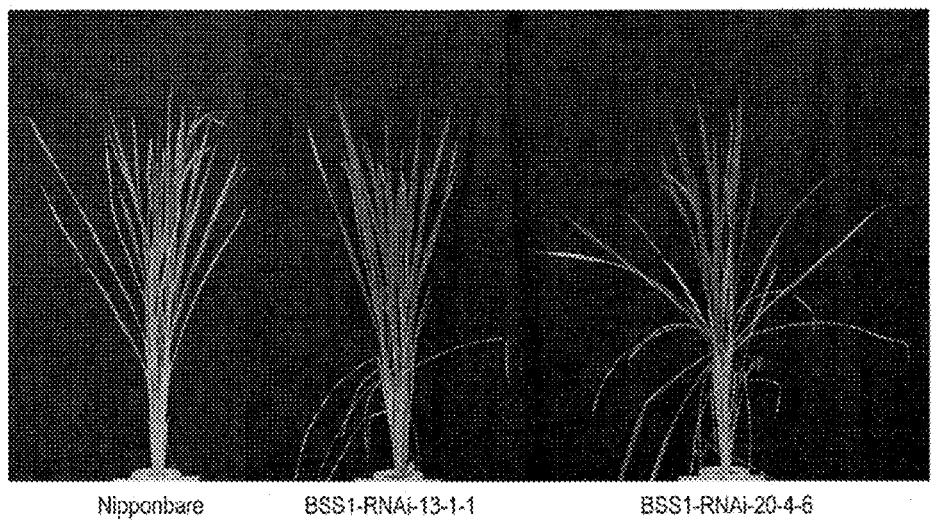
FIG. 14 shows phenotypes of wild-type rice (Nipponbare) and the rice BSS1-RNAi strain.
Figure 15:
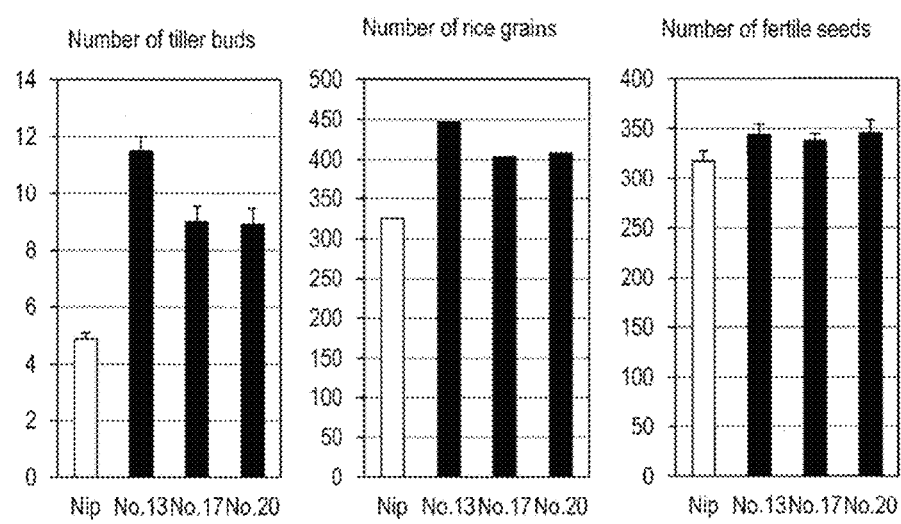
FIG. 15 shows the number of tiller buds, the number of rice grains, and the number of fertile seeds of the wild-type rice (Nipponbare) and the rice BSS1-RNAi strain.

Cloning of the amplified OsBSS1 was conducted using a pENTR/D TOPO cloning kit (Invitrogen). The prepared vector was introduced into rice (variety: Nipponbare) via the *Agrobacterium* EHA105 strain in accordance with the high-speed transformation method (Toki et al. Plant J. 47:969-76, 2006). The obtained transformant (BSS1-RNAi strain) had an increase in the number of tiller buds and a trait of tending to have an increase in lamina joint bending (FIG. 14). In addition, the obtained T1 generation and T2 homo generation transformants were examined in terms of yield trait. As a result, it was confirmed that the number of tiller buds, the number of rice grains, and the number of fertile seeds increased in both the T1 generation and the T2 homo generation (FIG. 15).

INDUSTRIAL APPLICABILITY

The present invention can be utilized in the field of breeding of transgenic plants having controlled plant lengths.

All publications, patents, and patent applications cited herein are incorporated herein by reference in their entirety.

The invention claimed is:

1. A method for producing a plant having increased biomass, which comprises the following steps:
   (1) transforming a plant of interest by suppressing expression of BSS1 gene in a plant body, or by disrupting said gene present in a plant body, or by inhibiting activity of said gene in a plant, and
   (2) comparing the transformed plant obtained in step (1) with a control wild-type plant, and selecting the transformed plant exhibiting at least one trait of promotion of plant length or stem length elongation, promotion of vascular bundle differentiation, petiole elongation, or leaf epinasty, based on the comparison.

2. The method according to claim 1, wherein the plant is in the form of a plant body, a plant organ, a plant tissue, or cultured plant cells.

3. The method according to claim 1, wherein the plant is a monocotyledonous plant or a dicotyledonous plant.

4. A plant having increased biomass produced by the method according to claim 1.

5. A method for producing a growth regulated plant having increased biomass, which comprises the following steps:
   (1) transforming a plant of interest by suppressing expression of any one of the following genes (a) to (f) in a plant body, or by disrupting said genes present in a plant body, or by inhibiting activity of said genes in a plant body,
      (a) a gene comprising DNA that consists of the nucleotide sequence shown in SEQ ID NO: 2 or 5;
      (b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;
      (c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;
      (d) a gene encoding a protein that consists of the amino acid sequence shown in SEQ ID NO: 3 or 6;
      (e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and
      (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling, and (2) comparing the transformed plant obtained in step (1) with a control wild-type plant, and selecting the transformed plant exhibiting at least one trait of promotion of plant length or stem length elongation, promotion of vascular bundle differentiation, petiole elongation, or leaf epinasty, based on the comparison.

6. A method for increasing biomass of a plant, which comprises the following steps:
(1) transforming a plant of interest by suppressing expression of any one of the following genes (a) to (f) in a plant body, or by disrupting said genes present in a plant body, or by inhibiting activity of said genes in a plant body,
  (a) a gene comprising DNA that consists of the nucleotide sequence shown in SEQ ID NO: 2 or 5;
  (b) a gene comprising DNA that hybridizes under stringent conditions to DNA consisting of a nucleotide sequence complementary to DNA consisting of the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;
  (c) a gene comprising DNA that consists of a nucleotide sequence having 60% or higher sequence identity with the nucleotide sequence shown in SEQ ID NO: 2 or 5, and encodes a protein having activity to bind to a brassinosteroid master transcription factor BIL1 protein to inhibit the transfer of the BIL1 protein into the nucleus, thereby down-regulating brassinosteroid signaling;
  (d) a gene encoding a protein that consists of the amino acid sequence shown in SEQ ID NO: 3 or 6;
  (e) a gene encoding a protein that consists of an amino acid sequence derived from the amino acid sequence shown in SEQ ID NO: 3 or 6 by deletion, substitution, or addition of 1 or several amino acids, and has activity to bind to a brassinosteroid master transcription factor BIL1 protein to inhibit the transfer of the BIL1 protein into the nucleus, thereby down-regulating brassinosteroid signaling; and
  (f) a gene encoding a protein that consists of an amino acid sequence having 60% or higher sequence identity with the amino acid sequence shown in SEQ ID NO: 3 or 6, and has activity to bind to a brassinosteroid master transcription factor BIL1 protein to inhibit the transfer of the BIL1 protein into the nucleus, thereby down-regulating brassinosteroid signaling, and (2) comparing the transformed plant obtained in step (1) with a control wild-type plant, and selecting the transformed plant exhibiting at least one trait of promotion of plant length or stem length elongation, promotion of vascular bundle differentiation, petiole elongation, or leaf epinasty, based on the comparison.

7. The method according to claim 6, wherein the plant is rice, and the increasing biomass is the increased number of tiller buds, the increased number of rice grains, or the increased number of fertile seeds.

8. The method according to claim 6, wherein the plant is a monocotyledonous plant or a dicotyledonous plant.

* * * * *